United States Patent
Cho et al.

(10) Patent No.: US 11,554,140 B2
(45) Date of Patent: *Jan. 17, 2023

(54) NUCLEIC ACID, CHIMERIC ANTIGEN RECEPTOR EXPRESSION PLASMID, CHIMERIC ANTIGEN RECEPTOR EXPRESSING CELL, USE THEREOF, AND PHARMACEUTICAL COMPOSITION FOR TREATING CANCER

(71) Applicant: China Medical University Hospital, Taichung (TW)

(72) Inventors: Der-Yang Cho, Taichung (TW); Shao-Chih Chiu, Taichung (TW); Chia-Ing Jan, Taichung (TW); Chih-Ming Pan, Taichung (TW); Shi-Wei Huang, Taichung (TW)

(73) Assignee: China Medical University Hospital, Taichung (TW)

( * ) Notice: Subject to any disclaimer, the term of this patent is extended or adjusted under 35 U.S.C. 154(b) by 601 days.

This patent is subject to a terminal disclaimer.

(21) Appl. No.: 16/390,359

(22) Filed: Apr. 22, 2019

(65) Prior Publication Data

US 2020/0216543 A1 Jul. 9, 2020

(30) Foreign Application Priority Data

Sep. 17, 2018 (TW) ................. 107132664

(51) Int. Cl.
| | | |
|---|---|---|
| A61K 39/00 | (2006.01) | |
| C07K 16/28 | (2006.01) | |
| A61K 35/17 | (2015.01) | |
| A61P 35/00 | (2006.01) | |
| A61K 31/282 | (2006.01) | |
| A61K 31/4188 | (2006.01) | |
| A61K 31/704 | (2006.01) | |
| A61K 31/7068 | (2006.01) | |
| C12N 5/0783 | (2010.01) | |
| C12N 9/22 | (2006.01) | |
| C07K 14/74 | (2006.01) | |

(52) U.S. Cl.
CPC ............ *A61K 35/17* (2013.01); *A61K 31/282* (2013.01); *A61K 31/4188* (2013.01); *A61K 31/704* (2013.01); *A61K 31/7068* (2013.01); *A61K 39/0011* (2013.01); *A61P 35/00* (2018.01); *C07K 14/70539* (2013.01); *C07K 16/2833* (2013.01); *C12N 5/0646* (2013.01); *C12N 9/22* (2013.01); *A61K 2039/5156* (2013.01); *A61K 2039/5158* (2013.01); *C07K 2317/565* (2013.01); *C07K 2319/00* (2013.01); *C12N 2510/00* (2013.01); *C12N 2800/80* (2013.01)

(58) Field of Classification Search
None
See application file for complete search history.

(56) References Cited

FOREIGN PATENT DOCUMENTS

| | | |
|---|---|---|
| JP | 2017534261 A | 11/2017 |
| JP | 2018511319 A | 4/2018 |
| WO | 2016044605 A1 | 3/2016 |
| WO | 2016160622 A2 | 10/2016 |
| WO | 2018057904 A1 | 3/2018 |

OTHER PUBLICATIONS

June et al (Science, 2018, 359: 1361-1365) (Year: 2018).*
Ramakrishna et al (Expert Opinion on Biological Therapy, 2020, 20(5): 503-516) (Year: 2020).*
Jan et al (Proc. AACR Special Conf. on Tumor Immunology and Immunotherapy, Nov. 17, 2019 , Cancer Immunol. Res. 2020, 8(3 Suppl): Abstract nr A61) (Year: 2020).*
Rouas-Freiss, Nathalie , et al., "The Dual Role of HLA-G in Cancer", Journal of Immunology Research, published on Mar. 31, 2014, vol. 2014, Article ID 359748, pp. 1-10, published by Hindawi Publishing Corporation, Egypt.

* cited by examiner

*Primary Examiner* — G. R. Ewoldt
*Assistant Examiner* — Marianne Dibrino

(57) ABSTRACT

The present disclosure relates to a chimeric antigen receptor, a nucleic acid, a chimeric antigen receptor expression plasmid, a chimeric antigen receptor expressing cell, a pharmaceutical composition for treating cancer, and use of the chimeric antigen receptor expressing cell. The chimeric antigen receptor is specific to human leukocyte antigen G. The nucleic acid encodes the chimeric antigen receptor. The chimeric antigen receptor expression plasmid expresses the chimeric antigen receptor. The chimeric antigen receptor expressing cell is obtained by transducing the chimeric antigen receptor into an immune cell. The pharmaceutical composition for treating cancer includes the chimeric antigen receptor expressing cell and a pharmaceutically acceptable carrier.

5 Claims, 33 Drawing Sheets

Specification includes a Sequence Listing.

```
                            SEQUENCE LISTING

<160> NUMBER OF SEQ ID NOS: 17

<210> SEQ ID NO 1
<211> LENGTH: 246
<212> TYPE: PRT
<213> ORGANISM: Artificial Sequence
<220> FEATURE:
<223> OTHER INFORMATION: anti-HLA-G antibody

<400> SEQUENCE: 1

Glu Val Gln Leu Gln Glu Ser Gly Gly Gly Leu Val Gln Pro Lys Gly
1               5                   10                  15

Ser Leu Lys Leu Ser Cys Ala Ala Phe Gly Phe Thr Phe Asn Thr Tyr
            20                  25                  30

Ala Met His Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Ser Leu Gln Met Asn Asn Leu Lys Thr Glu Asp Thr Ala Ile Tyr
                85                  90                  95

Tyr Cys Val Arg Gly Gly Tyr Trp Ser Phe Asp Val Trp Gly Ala Gly
            100                 105                 110

Thr Thr Val Thr Val Ser Ser Gly Gly Gly Ser Gly Gly Gly
            115                 120                 125

Ser Gly Gly Gly Gly Ser Asp Ile Val Ile Thr Gln Thr Thr Pro Ser
        130                 135                 140

Val Pro Val Thr Pro Gly Glu Ser Val Ser Ile Ser Cys Arg Ser Ser
145                 150                 155                 160

Lys Ser Leu Leu His Ser Asn Gly Asn Thr Tyr Leu Tyr Trp Phe Leu
                165                 170                 175

Gln Arg Pro Gly Gln Ser Pro Gln Leu Leu Ile Ser Arg Met Ser Ser
            180                 185                 190

Leu Ala Ser Gly Val Pro Asp Arg Phe Ser Gly Ser Gly Ser Gly Thr
        195                 200                 205

Ala Phe Thr Leu Arg Ile Ser Arg Val Glu Ala Glu Asp Val Gly Val
    210                 215                 220

Tyr Tyr Cys Met Gln His Leu Glu Tyr Pro Tyr Thr Phe Gly Gly Gly
225                 230                 235                 240

Thr Lys Leu Glu Ile Lys
                245

<210> SEQ ID NO 2
<211> LENGTH: 75
<212> TYPE: PRT
<213> ORGANISM: Artificial Sequence
<220> FEATURE:
<223> OTHER INFORMATION: HLA-G receptor

<400> SEQUENCE: 2

Ser Pro Thr Glu Pro Ser Ser Lys Thr Gly Asn Pro Arg His Leu His
1               5                   10                  15
```

```
Val Leu Ile Gly Thr Ser Val Val Lys Ile Pro Phe Thr Ile Leu Leu
            20                  25                  30

Phe Phe Leu Leu His Arg Trp Cys Ser Asn Lys Lys Asn Ala Ala Val
            35                  40                  45

Met Asp Gln Glu Pro Ala Gly Asn Arg Thr Val Asn Ser Glu Asp Ser
 50                  55                  60

Asp Glu Gln Asp His Gln Glu Val Ser Tyr Ala
 65                  70                  75

<210> SEQ ID NO 3
<211> LENGTH: 113
<212> TYPE: PRT
<213> ORGANISM: Artificial Sequence
<220> FEATURE:
<223> OTHER INFORMATION: costimulatory domain

<400> SEQUENCE: 3

Met Gly Gly Leu Glu Pro Cys Ser Arg Leu Leu Leu Leu Pro Leu Leu
 1               5                  10                  15

Leu Ala Val Ser Gly Leu Arg Pro Val Gln Ala Gln Ala Gln Ser Asp
            20                  25                  30

Cys Ser Cys Ser Thr Val Ser Pro Gly Val Leu Ala Gly Ile Val Met
            35                  40                  45

Gly Asp Leu Val Leu Thr Val Leu Ile Ala Leu Ala Val Tyr Phe Leu
 50                  55                  60

Gly Arg Leu Val Pro Arg Gly Arg Gly Ala Ala Glu Ala Ala Thr Arg
 65                  70                  75                  80

Lys Gln Arg Ile Thr Glu Thr Glu Ser Pro Tyr Gln Glu Leu Gln Gly
            85                  90                  95

Gln Arg Ser Asp Val Tyr Ser Asp Leu Asn Thr Gln Arg Pro Tyr Tyr
            100                 105                 110

Lys

<210> SEQ ID NO 4
<211> LENGTH: 439
<212> TYPE: PRT
<213> ORGANISM: Artificial Sequence
<220> FEATURE:
<223> OTHER INFORMATION: suicide protein

<400> SEQUENCE: 4

Met Gly Val Gln Val Glu Thr Ile Ser Pro Gly Asp Gly Arg Thr Phe
 1               5                  10                  15

Pro Lys Arg Gly Gln Thr Cys Val Val His Tyr Thr Gly Met Leu Glu
            20                  25                  30

Asp Gly Lys Lys Val Asp Ser Ser Arg Asp Arg Asn Lys Pro Phe Lys
            35                  40                  45

Phe Met Leu Gly Lys Gln Glu Val Ile Arg Gly Trp Glu Glu Gly Val
 50                  55                  60

Ala Gln Met Ser Val Gly Gln Arg Ala Lys Leu Thr Ile Ser Pro Asp
 65                  70                  75                  80

Tyr Ala Tyr Gly Ala Thr Gly His Pro Gly Ile Ile Pro Pro His Ala
            85                  90                  95

Thr Leu Val Phe Asp Val Glu Leu Leu Lys Leu Glu Ser Gly Gly Gly
            100                 105                 110

Ser Thr Asn Arg Gln Ala Ala Lys Leu Ser Lys Pro Thr Leu Glu Asn
            115                 120                 125
```

```
Leu Thr Pro Val Val Leu Arg Pro Glu Ile Arg Lys Pro Glu Val Leu
            130                 135                 140
Arg Pro Glu Thr Pro Arg Pro Val Asp Ile Gly Ser Gly Gly Phe Gly
145                 150                 155                 160
Asp Val Gly Ala Leu Glu Ser Leu Arg Gly Asn Ala Asp Leu Ala Tyr
                165                 170                 175
Ile Leu Ser Met Glu Pro Cys Gly His Cys Leu Ile Ile Asn Asn Val
            180                 185                 190
Asn Phe Cys Arg Glu Ser Gly Leu Arg Thr Arg Thr Gly Ser Asn Ile
        195                 200                 205
Asp Cys Glu Lys Leu Arg Arg Arg Phe Ser Ser Leu His Phe Met Val
    210                 215                 220
Glu Val Lys Gly Asp Leu Thr Ala Lys Lys Met Val Leu Ala Leu Leu
225                 230                 235                 240
Glu Leu Ala Gln Gln Asp His Gly Ala Leu Asp Cys Cys Val Val Val
                245                 250                 255
Ile Leu Ser His Gly Cys Gln Ala Ser His Leu Gln Phe Pro Gly Ala
            260                 265                 270
Val Tyr Gly Thr Asp Gly Cys Pro Val Ser Val Glu Lys Ile Val Asn
        275                 280                 285
Ile Phe Asn Gly Thr Ser Cys Pro Ser Leu Gly Gly Lys Pro Lys Leu
    290                 295                 300
Phe Phe Ile Gln Ala Cys Gly Gly Glu Gln Lys Asp His Gly Phe Glu
305                 310                 315                 320
Val Ala Ser Thr Ser Pro Glu Asp Glu Ser Pro Gly Ser Asn Pro Glu
                325                 330                 335
Pro Asp Ala Thr Pro Phe Gln Glu Gly Leu Arg Thr Phe Asp Gln Leu
            340                 345                 350
Asp Ala Ile Ser Ser Leu Pro Thr Pro Ser Asp Ile Phe Val Ser Tyr
        355                 360                 365
Ser Thr Phe Pro Gly Phe Val Ser Trp Arg Asp Pro Lys Ser Gly Ser
    370                 375                 380
Trp Tyr Val Glu Thr Leu Asp Asp Ile Phe Glu Gln Trp Ala His Ser
385                 390                 395                 400
Glu Asp Leu Gln Ser Leu Leu Leu Arg Val Ala Asn Ala Val Ser Val
                405                 410                 415
Lys Gly Ile Tyr Lys Gln Met Pro Gly Cys Phe Asn Phe Leu Arg Lys
            420                 425                 430
Lys Leu Phe Phe Lys Thr Ser
        435

<210> SEQ ID NO 5
<211> LENGTH: 8
<212> TYPE: PRT
<213> ORGANISM: Artificial Sequence
<220> FEATURE:
<223> OTHER INFORMATION: CDRH1

<400> SEQUENCE: 5

Gly Phe Thr Phe Asn Thr Tyr Ala
1               5

<210> SEQ ID NO 6
<211> LENGTH: 10
<212> TYPE: PRT
<213> ORGANISM: Artificial Sequence
```

```
<220> FEATURE:
<223> OTHER INFORMATION: CDRH2

<400> SEQUENCE: 6

Ile Arg Ser Lys Ser Asn Asn Tyr Ala Thr
1               5                   10

<210> SEQ ID NO 7
<211> LENGTH: 10
<212> TYPE: PRT
<213> ORGANISM: Artificial Sequence
<220> FEATURE:
<223> OTHER INFORMATION: CDRH3

<400> SEQUENCE: 7

Val Arg Gly Gly Tyr Trp Ser Phe Asp Val
1               5                   10

<210> SEQ ID NO 8
<211> LENGTH: 11
<212> TYPE: PRT
<213> ORGANISM: Artificial Sequence
<220> FEATURE:
<223> OTHER INFORMATION: CDRL2

<400> SEQUENCE: 8

Lys Ser Leu Leu His Ser Asn Gly Asn Thr Tyr
1               5                   10

<210> SEQ ID NO 9
<211> LENGTH: 9
<212> TYPE: PRT
<213> ORGANISM: Artificial Sequence
<220> FEATURE:
<223> OTHER INFORMATION: CDRL3

<400> SEQUENCE: 9

Met Gln His Leu Glu Tyr Pro Tyr Thr
1               5

<210> SEQ ID NO 10
<211> LENGTH: 22
<212> TYPE: PRT
<213> ORGANISM: Artificial Sequence
<220> FEATURE:
<223> OTHER INFORMATION: P2A

<400> SEQUENCE: 10

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 11
<211> LENGTH: 738
<212> TYPE: DNA
<213> ORGANISM: Artificial Sequence
<220> FEATURE:
<223> OTHER INFORMATION: anti-HLA-G antibody coding fragment

<400> SEQUENCE: 11
gaggttcagc tgcaagagtc tggcggagga ctggtgcagc ctaagggaag cctgaagctg      60
agctgtgccg ccttcggctt caccttcaac acctacgcca tgcactgggt ccgacaggcc     120
cctggaaaag gccttgaatg ggtcgcccgg atcagaagca gagcaacaa ttacgccacc     180
```

| | |
|---|---|
| tactacgccg acagcgtgaa ggacagattc accatcagcc gggacgacag ccagagcatg | 240 |
| ctgagcctgc agatgaacaa cctgaaaacc gaggacaccg ccatctacta ctgcgtcaga | 300 |
| ggcggctact ggtccttcga tgtttgggga gccggcacca ccgtgacagt ttctagcgga | 360 |
| ggcggtggat ctggcggcgg aggaagtggt ggcggaggtt ctgatatcgt gatcacccag | 420 |
| accacaccta gcgtgccagt gacacctggc gagagcgtgt ccatcagctg cagaagcagc | 480 |
| aagagcctgc tgcacagcaa cggcaatacc tacctgtact ggttcctgca gaggcccgga | 540 |
| cagtctcctc agctgctgat ctccagaatg agcagcctgg ctagcggcgt gcccgataga | 600 |
| ttttctggca gcggctctgg caccgccttc acactgagaa tcagcagagt ggaagccgag | 660 |
| gacgtgggcg tgtactactg tatgcagcac ctggaatacc cctacacctt cggcggaggc | 720 |
| accaagctgg aaatcaag | 738 |

<210> SEQ ID NO 12
<211> LENGTH: 225
<212> TYPE: DNA
<213> ORGANISM: Artificial Sequence
<220> FEATURE:
<223> OTHER INFORMATION: HLA-G receptor coding fragment

<400> SEQUENCE: 12

| | |
|---|---|
| tcacccactg aaccaagctc caaaaccggt aaccccagac acctgcatgt tctgattggg | 60 |
| acctcagtgg tcaaaatccc tttcaccatc ctcctcttct ttctccttca tcgctggtgc | 120 |
| tccaacaaaa aaaatgctgc tgtaatggac caagagcctg cagggaacag aacagtgaac | 180 |
| agcgaggatt ctgatgaaca agaccatcag gaggtgtcat acgca | 225 |

<210> SEQ ID NO 13
<211> LENGTH: 339
<212> TYPE: DNA
<213> ORGANISM: Artificial Sequence
<220> FEATURE:
<223> OTHER INFORMATION: costimulatory domain coding fragment

<400> SEQUENCE: 13

| | |
|---|---|
| atgggggac ttgaaccctg cagcaggctc ctgctcctgc ctctcctgct ggctgtaagt | 60 |
| ggtctccgtc ctgtccaggc ccaggcccag agcgattgca gttgctctac ggtgagcccg | 120 |
| ggcgtgctgg cagggatcgt gatgggagac ctggtgctga cagtgctcat tgccctggcc | 180 |
| gtgtacttcc tgggccggct ggtccctcgg gggcgagggg ctgcggaggc agcgacccgg | 240 |
| aaacagcgta tcactgagac cgagtcgcct tatcaggagc tccagggtca gaggtcggat | 300 |
| gtctacagcg acctcaacac acagaggccg tattacaaa | 339 |

<210> SEQ ID NO 14
<211> LENGTH: 1317
<212> TYPE: DNA
<213> ORGANISM: Artificial Sequence
<220> FEATURE:
<223> OTHER INFORMATION: suicide gene

<400> SEQUENCE: 14

| | |
|---|---|
| atgggagtgc aggtggaaac catctcccca ggagacgggc gcaccttccc caagcgcggc | 60 |
| cagacctgcg tggtgcacta caccgggatg cttgaagatg gaaagaaagt ggattcctcc | 120 |
| cgggacagaa acaagccctt taagtttatg ctaggcaagc aggaggtgat ccgaggctgg | 180 |
| gaagaagggg ttgcccagat gagtgtgggt cagagagcca aactgactat atctccagat | 240 |
| tatgcctatg gtgccactgg gcacccaggc atcatcccac acatgccac tctcgtcttc | 300 |

```
gatgtggagc ttctaaaact ggaatctgga ggaggttcta ctaacaggca agcagcaaag      360
ttgtcgaagc caaccctaga aaaccttacc ccagtggtgc tcagaccaga gattcgcaaa      420
ccagaggttc tcagaccgga acacccaga ccagtggaca ttggttctgg aggatttggt       480
gatgtcggtc tcttgagag tttgagggga aatgcagatt tggcttacat cctgagcatg      540
gagccctgtg ccactgcct cattatcaac aatgtgaact ctgccgtga gtccgggctc        600 cgcacccgca ctggctccaa catcgactgt gagaagttgc ggcgtcgctt ctcctcgctg      660
catttcatgg tggaggtgaa gggcgacctg actgccaaga aaatggtgct ggctttgctg      720
gagctggcgc agcaggacca cggtgctctg gactgctgcg tggtggtcat tctctctcac      780
ggctgtcagg ccagccacct gcagttccca ggggctgtct acggcacaga tggatgccct      840
gtgtcggtcg agaagattgt gaacatcttc aatgggacca gctgccccag cctgggaggg      900
aagcccaagc tctttttcat ccaggcctgt ggtggggagc agaaagacca tgggtttgag      960
gtggcctcca cttccctga agacgagtcc cctggcagta accccgagcc agatgccacc     1020
ccgttccagg aaggtttgag gaccttcgac cagctggacg ccatatctag tttgcccaca     1080
cccagtgaca tctttgtgtc ctactctact ttcccaggtt ttgtttcctg gagggacccc     1140
aagagtggct cctggtacgt tgagaccctg gacgacatct ttgagcagtg ggctcactct     1200
gaagacctgc agtccctcct gcttagggtc gctaatgctg tttcggtgaa agggattat     1260 aaacagatgc ctggttgctt taattcctc cggaaaaaac ttttctttaa aacatca        1317

<210> SEQ ID NO 15
<211> LENGTH: 66
<212> TYPE: DNA
<213> ORGANISM: Artificial Sequence
<220> FEATURE:
<223> OTHER INFORMATION: 2A peptide coding fragment

<400> SEQUENCE: 15
ggatctggcg ccaccaactt cagcctgctg aagcaggcag gcgacgtgga agagaaccct      60
ggccct                                                                66

<210> SEQ ID NO 16
<211> LENGTH: 1335
<212> TYPE: DNA
<213> ORGANISM: Artificial Sequence
<220> FEATURE:
<223> OTHER INFORMATION: promoter

<400> SEQUENCE: 16
gagtaattca tacaaaagga ctcgcccctg ccttggggaa tcccagggac cgtcgttaaa      60 ctccccactaa cgtagaaccc agatcgcgt gcgttcccgc ccctcaccc gcccgctctc      120 gtcatcactg aggtggagaa gagcatgcgt gaggctccgg tgcccgtcag tgggcagagc     180
gcacatcgcc cacagtcccc gagaagttgg ggggagggg cggcaattga accggtgcct     240
agagaaggtg gcgcggggta aactgggaaa gtgatgtcgt gtactggctc cgcctttttc     300
ccgagggtgg gggagaaccg tatataagtg cagtagtcgc cgtgaacgtt cttttttcgca     360 acgggtttgc cgccagaaca caggtaagtg ccgtgtgtg ttcccgcggg cctgcctct       420 ttacgggtta tggcccttgc gtgccttgaa ttacttccac gccctggct gcagtacgtg     480 attcttgatc ccgagcttcg ggttggaagt gggtgggaga gttcgaggcc ttgcgcttaa     540
ggagcccctt cgcctcgtgc ttgagttgag gcctggcttg ggcgctgggg ccgccgcgtg      600
```

```
cgaatctggt ggcaccttcg cgcctgtctc gctgctttcg ataagtctct agccatttaa    660
aatttttgat gacctgctgc gacgctttttt ttctggcaag atagtcttgt aaatgcgggc    720
caagatctgc acactggtat ttcggttttt ggggccgcgg gcggcgacgg ggcccgtgcg    780
tcccagcgca catgttcggc gaggcggggc ctgcgagcgc ggccaccgag aatcggacgg    840
gggtagtctc aagctggccg gcctgctctg gtgcctggcc tcgcgccgcc gtgtatcgcc    900
ccgccctggg cggcaaggct ggcccggtcg gcaccagttg cgtgagcgga agatggccg    960 cttcccggcc ctgctgcagg gagctcaaaa tggaggacgg ggcgctcggg agagcgggcg   1020
ggtgagtcac ccacacaaag gaaaagggcc tttccgtcct cagccgtcgc ttcatgtgac   1080
tccacggagt accgggcgcc gtccaggcac ctcgattagt tctcgagctt ttggagtacg   1140
tcgtctttag gttggggga ggggttttat gcgatggagt ttccccacac tgagtgggtg    1200
gagactgaag ttaggccagc ttggcacttg atgtaattct ccttggaatt tgccctttt   1260 gagtttggat cttggttcat tctcaagcct cagacagtgg ttcaaagttt ttttcttcca   1320
tttcaggtgt cgtga                                                   1335

<210> SEQ ID NO 17
<211> LENGTH: 63
<212> TYPE: DNA
<213> ORGANISM: Artificial Sequence
<220> FEATURE:
<223> OTHER INFORMATION: signal peptide

<400> SEQUENCE: 17
atggccctcc ctgtcaccgc cctgctgctt ccgctggctc ttctgctcca cgccgctcgg    60
ccc                                                                 63
```

NUCLEIC ACID, CHIMERIC ANTIGEN RECEPTOR EXPRESSION PLASMID, CHIMERIC ANTIGEN RECEPTOR EXPRESSING CELL, USE THEREOF, AND PHARMACEUTICAL COMPOSITION FOR TREATING CANCER

RELATED APPLICATIONS

This application claims priority to Taiwan Application Serial Number 107132664, filed Sep. 17, 2018, which is herein incorporated by reference.

SEQUENCE LISTING

The sequence listing submitted via EFS, in compliance with 37 CFR § 1.52(e)(5), is incorporated herein by reference. The sequence listing text file submitted via EFS contains the file "CP-4278-US_SequenceListing", created on Mar. 20, 2019, which is 15,965 bytes in size.

BACKGROUND

Technical Field

The present disclosure relates to a pharmaceutical product containing an antigen or an antibody. More particularly, the present disclosure relates to a chimeric antigen receptor, a nucleic acid encoding the chimeric antigen receptor, a chimeric antigen receptor expression plasmid, a chimeric antigen receptor expressing cell, a pharmaceutical composition for treating cancer, and use of the chimeric antigen receptor expressing cell.

Description of Related Art

Cancer, also known as malignancy, is a state of abnormal proliferation of cells, and these proliferating cells may invade other parts of the body as a disease caused by a malfunction in the control of cell division and proliferation. The number of people suffering from cancer worldwide has a growing trend. Cancer is one of the top ten causes of death for the Chinese people and has been the top ten causes of death for twenty-seven consecutive years.

Conventional cancer treatments include surgery, radiation therapy, chemotherapy, and target therapy. Cancer immunotherapy is another method for treating cancer except the above methods. The immune system of the patient is activated in the cancer immunotherapy by using tumor cells or tumor antigens to induce specific cellular and humoral immune responses for enhancing the anti-cancer ability of the patient, preventing the growth, spread, and recurrence of tumors, and achieving the purpose of removing or controlling tumors.

There are three main directions for the cancer immunotherapy: the tumor vaccine, the cell therapy and the immune checkpoint inhibitor. The chimeric antigen receptor immune cell technology is one of the cell therapy developing very rapidly in recent years. In conventional technology, the chimeric antigen receptor immune cell transfecting a chimeric protein, which couples the antigen binding portion having capable of recognizing a certain tumor antigen of the antibody to the intracellular portion of the CD3-δ chain or FcεRIγ in vitro, into the immune cell by a transduction method to express the chimeric antigen receptor. The chimeric antigen receptor immune cell technology has a significant therapeutic effect in the treatment of acute leukemia and non-Hodgkin's lymphoma, and it is considered to be one of the most promising treatment for cancer. However, the cell therapy of the chimeric antigen receptor immune cell currently has the following disadvantages: lack of unique tumor-associated antigens, low efficiency of homing of immune cells to tumor sites, and inability to overcome the immunosuppressive microenvironment of solid tumors. Accordingly, the efficacy of the chimeric antigen receptor immune cell in solid tumors is greatly limited.

SUMMARY

According to one aspect of the present disclosure, a chimeric antigen receptor specific to human leukocyte antigen G (HLA-G) includes, in order from an N-terminus to a C-terminus, an anti-HLA-G antibody including an amino acid sequence of SEQ ID NO: 1, an HLA-G receptor including an amino acid sequence of SEQ ID NO: 2, and a costimulatory domain including an amino acid sequence of SEQ ID NO: 3.

According to another aspect of the present disclosure, a nucleic acid encoding the chimeric antigen receptor according to the aforementioned aspect includes, in order from a 5' end to a 3' end, an anti-HLA-G antibody coding fragment including a nucleic acid sequence of SEQ ID NO: 11, an HLA-G receptor coding fragment including a nucleic acid sequence of SEQ ID NO: 12, and a costimulatory domain coding fragment including a nucleic acid sequence of SEQ ID NO: 13.

According to still another aspect of the present disclosure, a chimeric antigen receptor expression plasmid includes, in order from a 5' end to a 3' end, a promoter including a nucleic acid sequence of SEQ ID NO: 15 and the nucleic acid according to the foregoing aspect.

According to yet another aspect of the present disclosure, a chimeric antigen receptor expressing cell includes an immune cell and the chimeric antigen receptor expression plasmid according to the foregoing aspect.

According to further another aspect of the present disclosure, pharmaceutical composition for treating a cancer includes the chimeric antigen receptor expressing cell according to the foregoing aspect and a pharmaceutically acceptable carrier.

According to still another aspect of the present disclosure, a method for inhibiting a proliferation of a tumor cell includes administering a composition containing a plurality of the chimeric antigen receptor expressing cells according to the foregoing aspect to a subject in need for a treatment of a tumor.

BRIEF DESCRIPTION OF THE DRAWINGS

The present disclosure can be more fully understood by reading the following detailed description of the embodiment, with reference made to the accompanying drawings as follows.

DETAILED DESCRIPTION

A chimeric antigen receptor, a nucleic acid encoding the chimeric antigen receptor, a chimeric antigen receptor expression plasmid including the nucleic acid, a chimeric antigen receptor expressing cell including the chimeric antigen receptor expression plasmid, a use thereof, and a pharmaceutical composition for treating cancer including the chimeric antigen receptor expressing cell are provided. A tumor cell specific binding ability of the chimeric antigen receptor of the present disclosure, especially a specific binding ability to human leukocyte antigen G (HLA-G) expressed on the cell membrane of tumor cells, is confirmed by in vitro cell assay of the tumor cells. Accordingly, the chimeric antigen receptor expressing cell of the present disclosure, which expresses the chimeric antigen receptor of the present disclosure, can specifically target the tumor cells to avoid the off-target effect, thereby effectively killing the tumor cells. Therefore, the chimeric antigen receptor expressing cell can be used for inhibiting the proliferation of the tumor cells in a subject in need for a treatment of a tumor. The pharmaceutical composition for treating cancer of the present disclosure includes the chimeric antigen receptor expressing cell of the present disclosure, and can further include a chemotherapy drug, which can effectively kill tumor cells and thereby treat cancer.

The term "human leukocyte antigen G (HLA-G)" is a protein that in humans is encoded by the HLA-G gene. The HLA-G belongs to nonclassical class I major histocompatibility complex (MHC) with a heavy chain of approximately 45 kDa. HLA-G is expressed on fetal derived placental cells, and is active in the negative regulation of immune response. HLA-G may play a role in immune tolerance in pregnancy.

Reference will now be made in detail to the present embodiments of the present disclosure, examples of which are illustrated in the accompanying drawings.

EXAMPLES

Figure 1:
FIG. 1 is a schematic view showing a protein structure of an anti-HLA-G antibody according to one embodiment of the present disclosure.

I. Chimeric Antigen Receptor, Nucleic Acid and Chimeric Antigen Receptor Expression Plasmid of the Present Disclosure The chimeric antigen receptor of the present disclosure is specific to HLA-G, and includes, in order from an N-terminus to a C-terminus, an anti-HLA-G antibody including an amino acid sequence of SEQ ID NO: 1, an HLA-G receptor including an amino acid sequence of SEQ ID NO: 2, and a costimulatory domain including an amino acid sequence of SEQ ID NO: 3. Preferably, a suicide protein including an amino acid sequence of SEQ ID NO: 4 is linked to the C-terminus of the costimulatory domain, and a 2A peptide including an amino acid sequence of SEQ ID NO: 10 links the HLA-G receptor and the costimulatory domain. In detail, the anti-HLA-G antibody including the amino acid sequence of SEQ ID NO: 1 includes a heavy chain (HC) immunoglobulin variable domain sequence and a light chain (LC) immunoglobulin variable domain sequence. The HC immunoglobulin variable domain sequence includes a CDRH1 including an amino acid sequence of SEQ ID NO: 5, a CDRH2 including an amino acid sequence of SEQ ID NO: 6, and a CDRH3 including an amino acid sequence of SEQ ID NO: 7. The LC immunoglobulin variable domain sequence includes a CDRL2 including an amino acid sequence of SEQ ID NO: 8, and a CDRL3 including an amino acid sequence of SEQ ID NO: 9. Please refer to FIG. 1, which is a schematic view showing a protein structure of the anti-HLA-G antibody according to one embodiment of the present disclosure. The looped region in which the sprinkle is indicated represents the variable domain in the anti-HLA-G antibody of the present disclosure. The HLA-G receptor including an amino acid sequence of SEQ ID NO: 2 is killer cell immunoglobulin-like receptor 2DS4 (KIR2DS4). The costimulatory domain including an amino acid sequence of SEQ ID NO: 3 is DNAX activating protein 12 (DAP12). The suicide protein including an amino acid sequence of SEQ ID NO: 4 is iCas9 protein.

The nucleic acid of the present disclosure encodes the chimeric antigen receptor of the present disclosure. The nucleic acid includes, in order from a 5' end to a 3' end, an anti-HLA-G antibody coding fragment including a nucleic acid sequence of SEQ ID NO: 11, an HLA-G receptor coding fragment including a nucleic acid sequence of SEQ ID NO: 12, and a costimulatory domain coding fragment including a nucleic acid sequence of SEQ ID NO: 13. Preferably, a suicide gene including a nucleic acid sequence of SEQ ID NO: 14 is linked to the 3' end of the costimulatory domain coding fragment, and a 2A peptide coding fragment including a nucleic acid sequence of SEQ ID NO: 15 links the HLA-G receptor coding fragment and the costimulatory domain coding fragment. The anti-HLA-G antibody coding fragment including a nucleic acid sequence of SEQ ID NO: 11 encodes the anti-HLA-G antibody including an amino acid sequence of SEQ ID NO: 1. The HLA-G receptor coding fragment including a nucleic acid sequence of SEQ ID NO: 12 encodes the HLA-G receptor including an amino acid sequence of SEQ ID NO: 2. The costimulatory domain coding fragment including a nucleic acid sequence of SEQ ID NO: 13 encodes the costimulatory domain including an amino acid sequence of SEQ ID NO: 3. The suicide gene including a nucleic acid sequence of SEQ ID NO: 14 encodes the suicide protein including an amino acid sequence of SEQ ID NO: 4. The 2A peptide coding fragment including a nucleic acid sequence of SEQ ID NO: 15 encodes the 2A peptide including an amino acid sequence of SEQ ID NO: 10.

Figure 2:
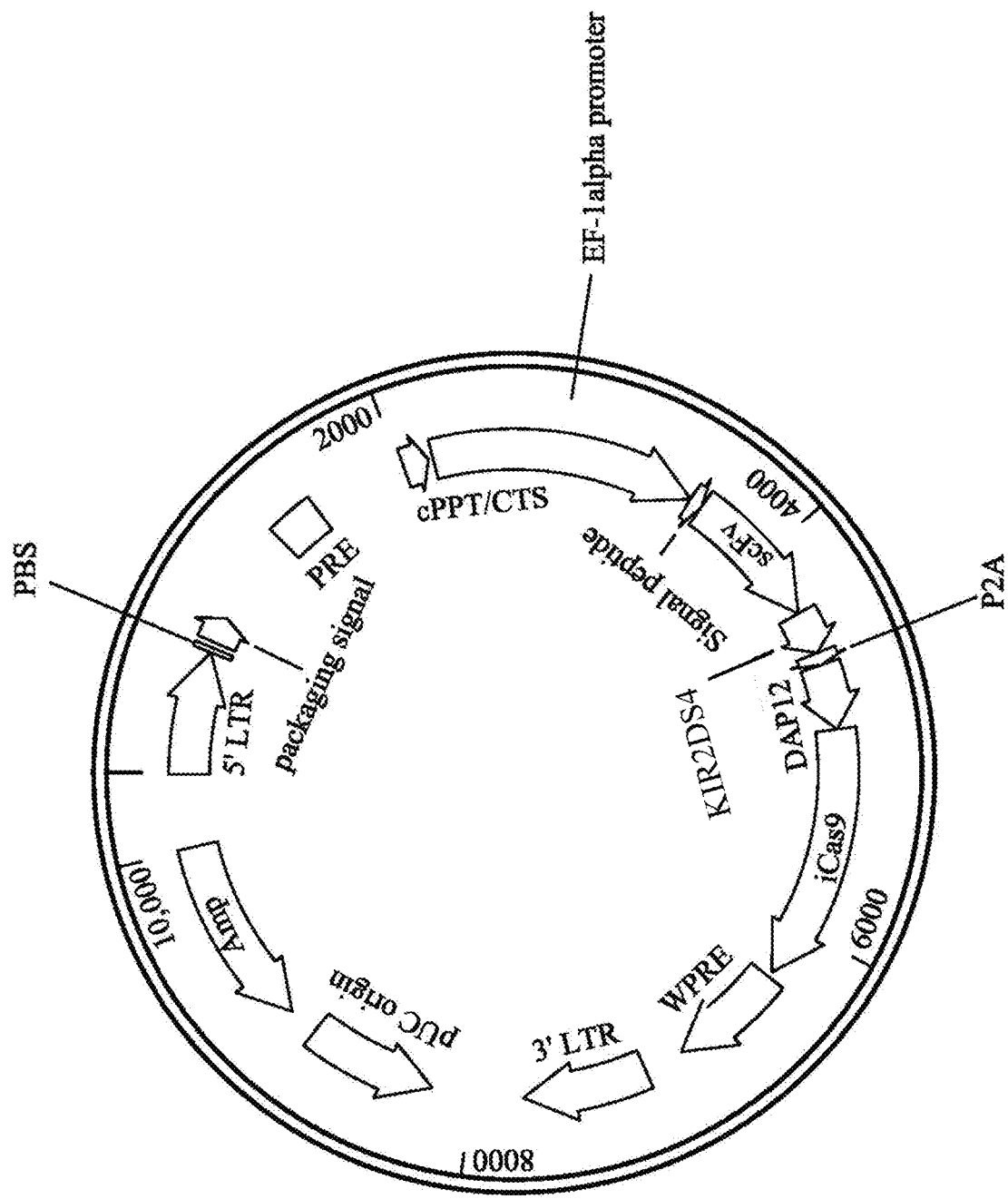
FIG. 2 is a schematic view showing a construction of a chimeric antigen receptor expression plasmid according to another embodiment of the present disclosure.

FIG. 2 is a schematic view showing a construction of a chimeric antigen receptor expression plasmid according to another embodiment of the present disclosure. In detail, according to one example of this embodiment, the chimeric antigen receptor expression plasmid is Lenti-EF1a-CAR-100517-S1A plasmid, wherein the insert thereof includes a promoter, an anti-HLA-G antibody coding fragment, an HLA-G receptor coding fragment, and a costimulatory domain coding fragment. The promoter is the EF-1 alpha promoter including a nucleic acid sequence of SEQ ID NO: 16. The anti-HLA-G antibody coding fragment includes the nucleic acid sequence of SEQ ID NO: 11. The HLA-G receptor coding fragment includes the nucleic acid sequence of SEQ ID NO: 12. The costimulatory domain coding fragment includes the nucleic acid sequence of SEQ ID NO: 13. In addition, the insert of the Lenti-EF1a-CAR-100517-S1A plasmid further includes a signal peptide coding fragment including a nucleic acid sequence of SEQ ID NO: 17, the suicide gene including the nucleic acid sequence of SEQ ID NO: 14, and the 2A peptide coding fragment including the nucleic acid sequence of SEQ ID NO: 15. The signal peptide coding fragment is linked to the 5' end of the anti-HLA-G antibody coding fragment, the suicide gene is linked to the 3' end of the costimulatory domain coding fragment, and the 2A peptide coding fragment links the HLA-G receptor coding fragment and the costimulatory domain coding fragment. Then, the insert is constructed on Creative Biolabs vector (Creative Biolabs, N.Y., USA) to obtain the Lenti-EF1a-CAR-100517-S1A plasmid. The Creative Biolabs vector is a lentivirus vector system, so that the constructed chimeric antigen receptor expression plasmid can be transfected into expression cells to produce lentiviruses, and the chimeric antigen receptor can be subsequently transduced into the immune cells using lentiviruses.

II. Chimeric Antigen Receptor Expressing Cell, Use thereof and Pharmaceutical Composition for Treating Cancer of the Present Disclosure The chimeric antigen receptor expressing cell of the present disclosure is obtained by transducing the chimeric antigen receptor of the present disclosure into the immune cell using lentiviruses. Preferably, the immune cell can be a T lymphocyte or a natural killer (NK) cell. More preferably, the NK cell can be a NK-92 cell line or a primary NK cell. In detail, the constructed Lenti-EF1a-CAR-100517-S1A plasmid is transfected into a 293T cell line using lipofectamine 3000 (Invitrogen) to prepare the lentiviruses carrying the chimeric antigen receptor of the present disclosure. For obtaining one example of the chimeric antigen receptor expressing cell, the supernatant containing the prepared lentiviruses and OPTI-MEM® (Invitrogen) containing 8 µg/ml of polybrene (Sigma-Aldrich) are used to culture the primary T lymphocytes for 3 days to transduce the chimeric antigen receptor of the present disclosure into the primary T lymphocytes. For obtaining another example of the chimeric antigen receptor expressing cell, the supernatant containing the prepared lentiviruses and the OPTI-MEM® (Invitrogen) containing 50 µg/ml of protamine sulfate (Sigma-Aldrich) are used to culture the primary NK cells or the NK-92 cell line for 7 days to transduce the chimeric antigen receptor of the present disclosure into the primary NK cell or the NK-92 cell line. The obtained chimeric antigen receptor expressing cell has an effect of inducing tumor cell death in mammals, so that the chimeric antigen receptor expressing cell can be used for inhibiting a proliferation of tumor cells in a subject in need for a treatment of a tumor. Preferably, the tumor cell can be a breast cancer cell, a polymorphic glioblastoma cell, a pancreatic cancer cell or an ovarian cancer cell.

The pharmaceutical composition for treating a cancer of the present disclosure includes the chimeric antigen receptor expressing cell of the present disclosure and a pharmaceutically acceptable carrier. Preferably, the pharmaceutical composition for treating cancer can further include a chemotherapy drug. More preferably, the chemotherapy drug can be doxorubicin (Dox), temozolomide (TMZ), gemcitabine (Gem) or carboplatin (CB).

The chimeric antigen receptor expressing cell and the pharmaceutical composition for treating the cancer will be further described by the following embodiments. In the following, an Example 1, an Example 2 and an Example 3 will be further provided to illustrate the accompanied efficacies of chimeric antigen receptor expressing cell and the pharmaceutical composition for treating the cancer on inducing tumor cell death. However, the present disclosure is not limited thereto. The tumor cells used are human breast cancer cell line MDA-MB-231, human malignant brain tumor cell line DBTRG-05MG (hereinafter referred to as DBTRG), human pancreatic cancer cell line AsPC1, and human ovarian cancer cell line SKOV3. The tumor cell lines used are all purchased from the American Type Culture Collection (ATCC). The human breast cancer cell line MDA-MB-231 is a triple-negative breast cancer cell line, that is, the hormone receptor (ER, PR) and HER-2 receptor thereof are negative, and the human breast cancer cell line MDA-MB-231 is cultured in RPMI culture medium containing 10% fetal bovine serum (FBS). The human malignant brain tumor cell line DBTRG is cultured in DMEM culture medium containing 10% FBS. The human pancreatic cancer cell line AsPC1 is cultured in RPMI culture medium containing 10% FBS. The human ovarian cancer cell line SKOV3 is cultured in McCoy's 5A culture medium containing 10% FBS.

2.1. Example 1

Figure 3:
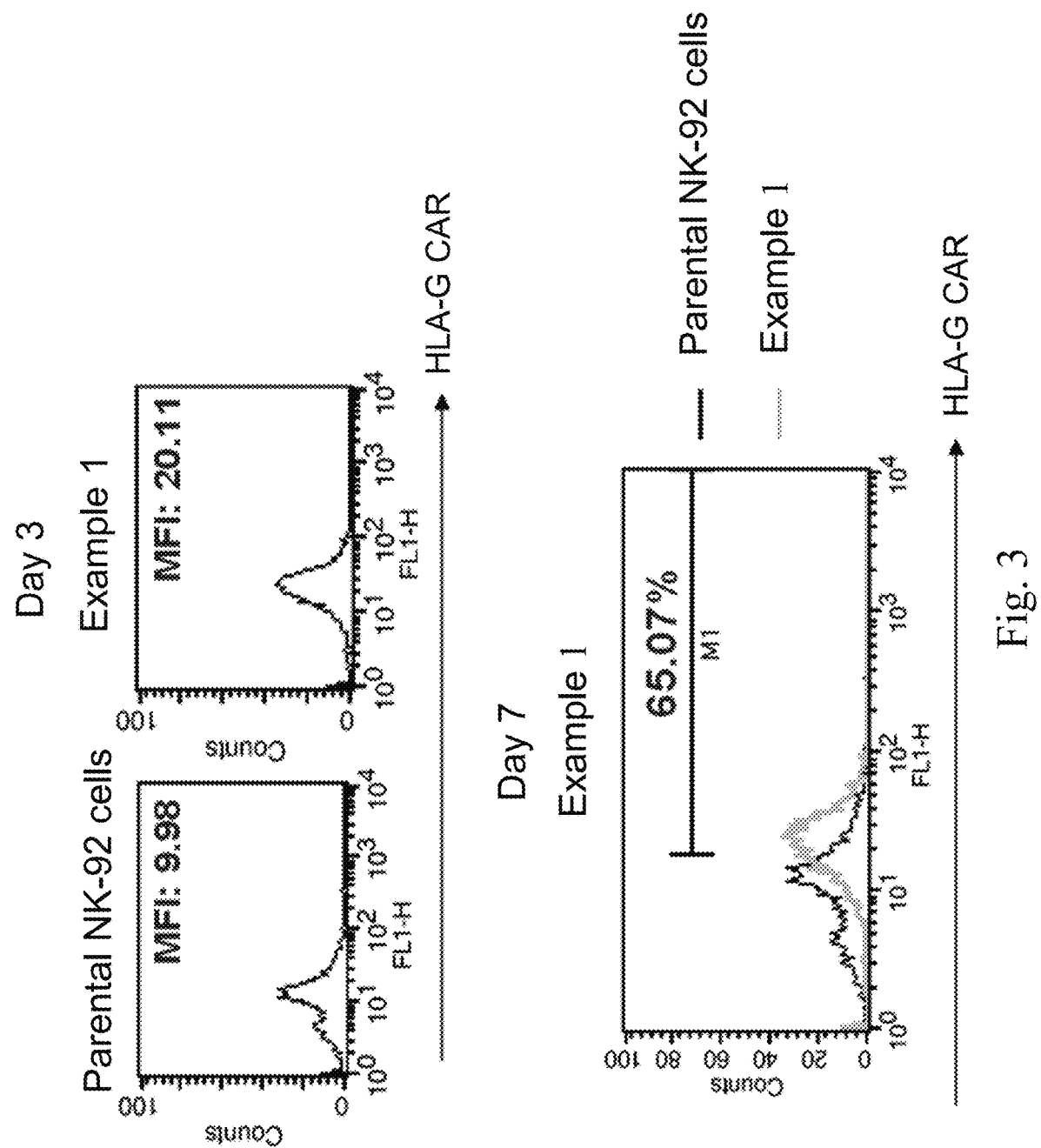
FIG. 3 is a graph showing an expression level of chimeric antigen receptors in a chimeric antigen receptor expressing cell according to Example 1 of the present disclosure.

The chimeric antigen receptor of the present disclosure is transduced into the NK-92 cell line to obtain the chimeric antigen receptor expressing cell of Example 1 of the present disclosure, and the expression level of the chimeric antigen receptor of the obtained chimeric antigen receptor expressing cell of Example 1 is analyzed by flow cytometry. Please refer to FIG. 3, which is a graph showing the expression level of chimeric antigen receptors in the chimeric antigen receptor expressing cell according to Example 1 of the present disclosure. FIG. 3 shows the expression level of the chimeric antigen receptor of the parental NK-92 cell line without transducing the chimeric antigen receptor of the present disclosure, and the expression level of the chimeric antigen receptor of the chimeric antigen receptor expressing cell of Example 1 on day 3 and day 7 after transduction the chimeric antigen receptor. In FIG. 3, the mean fluorescence intensity (MFI) of the parental NK-92 cell line is only 9.98%, while the MFI of the chimeric antigen receptor expressing cell of Example 1 on day 3 and day 7 after transduction can reach 20.11% and 65.07%, respectively. The results indicate that the chimeric antigen receptor expressing cell of Example 1 can stably express the chimeric antigen receptor of the present disclosure.

The effects of the chimeric antigen receptor expressing cell of Example 1 of the present disclosure on inducing the death of the breast cancer cells, the glioblastoma multiforme cells, the pancreatic cancer cells, and the ovarian cancer cells are further demonstrated in following experiments.

First, the human breast cancer cell line MDA-MB-231, the human malignant brain tumor cell line DBTRG, the human pancreatic cancer cell line AsPC1 and the human ovarian cancer cell line SKOV3 are seeded in a 12-well plate at a density of $1 \times 10^5$ cells/well. The cells are subsequently incubated for 24 hours. Each type of the tumor cells is divided into three groups. In a control, the tumor cells are untreated. In a group 1, the tumor cells are treated with the parental NK-92 cell line, and the number of the parental NK-92 cell line treated is $1\times10^5$ cells. In a group 2, the tumor cells are treated with the chimeric antigen receptor expressing cell of Example 1, and the number of the chimeric antigen receptor expressing cell of Example 1 treated is $1\times10^5$ cells. The treated cells are stained with Annexin V-FITC and propidium iodide (PI), and the apoptosis and the death of the tumor cells are detected by the flow cytometry. The sum of the percentage of cells stained with Annexin V-FITC and/or PI (that is the percentage of cells in the first quadrant, the second quadrant, and the fourth quadrant of the bivariate flow cytometry scatter plot) are calculated to obtain the cytotoxicity. The results of the cytotoxicity are counted after the three independent trials in each group.

Figure 4A:
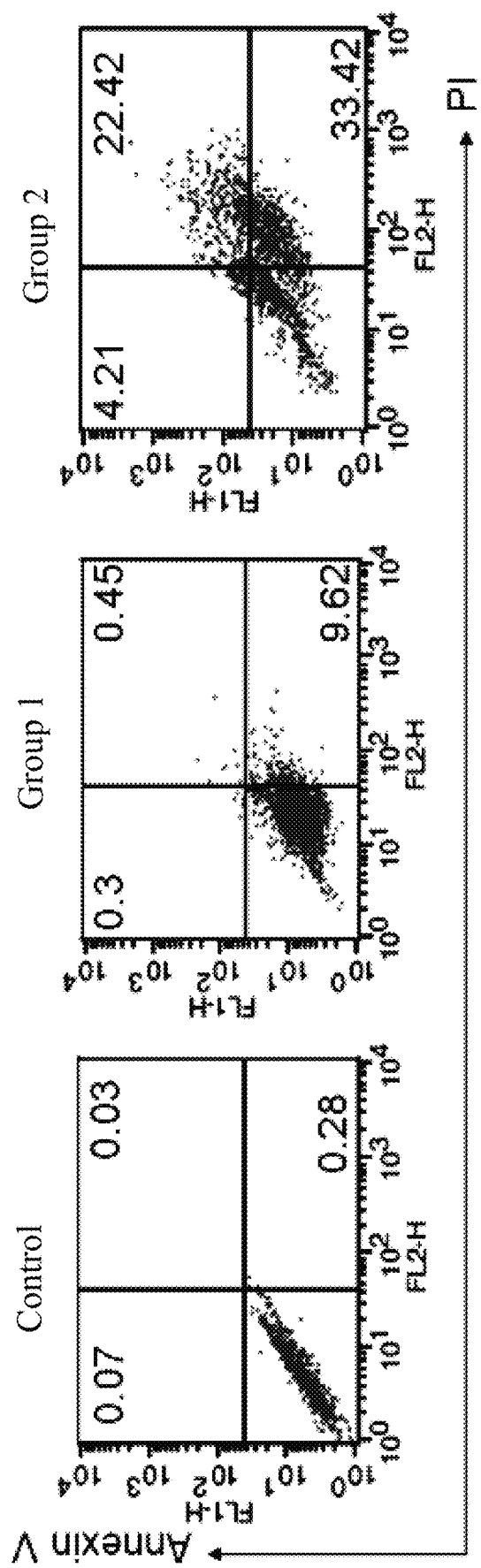
FIGS. 4A, 4B, 4C, 4D, 4E, 4F, 4G, 4H and 4I show analytical results of tumor cell death induced by chimeric antigen receptor expressing cells according to Example 1 of the present disclosure.
Figure 4B:
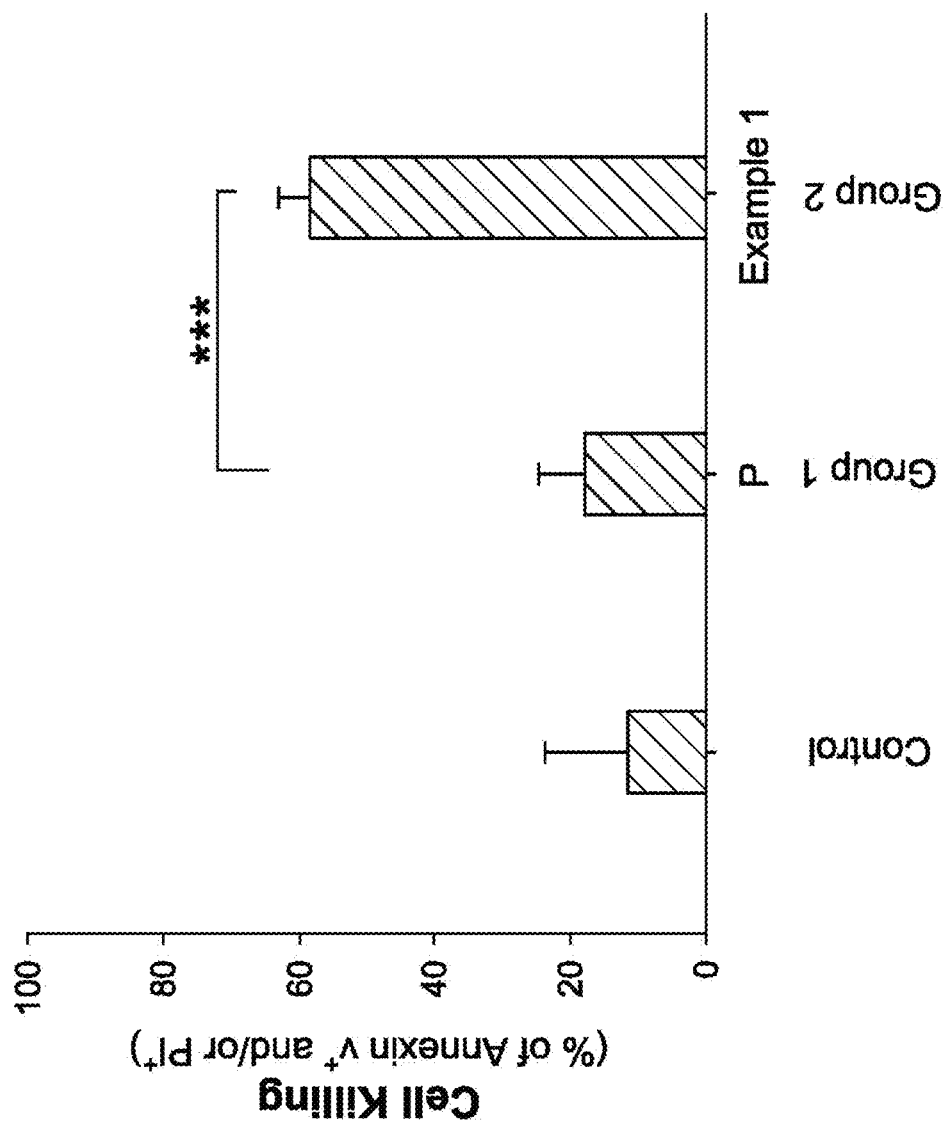
Figure 4C:
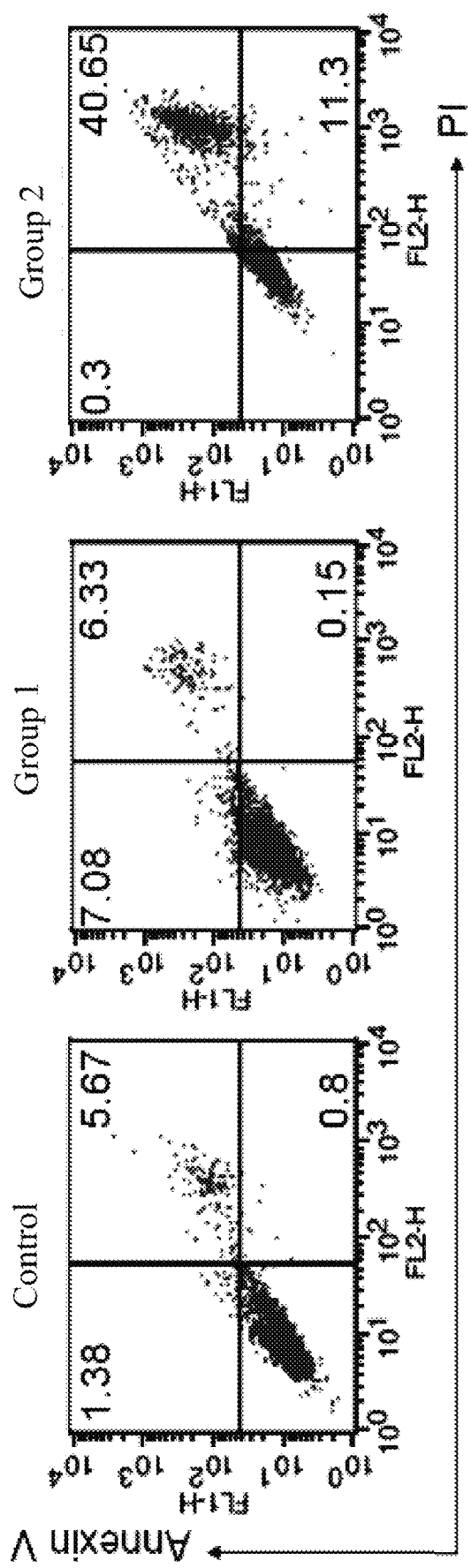
Figure 4D:
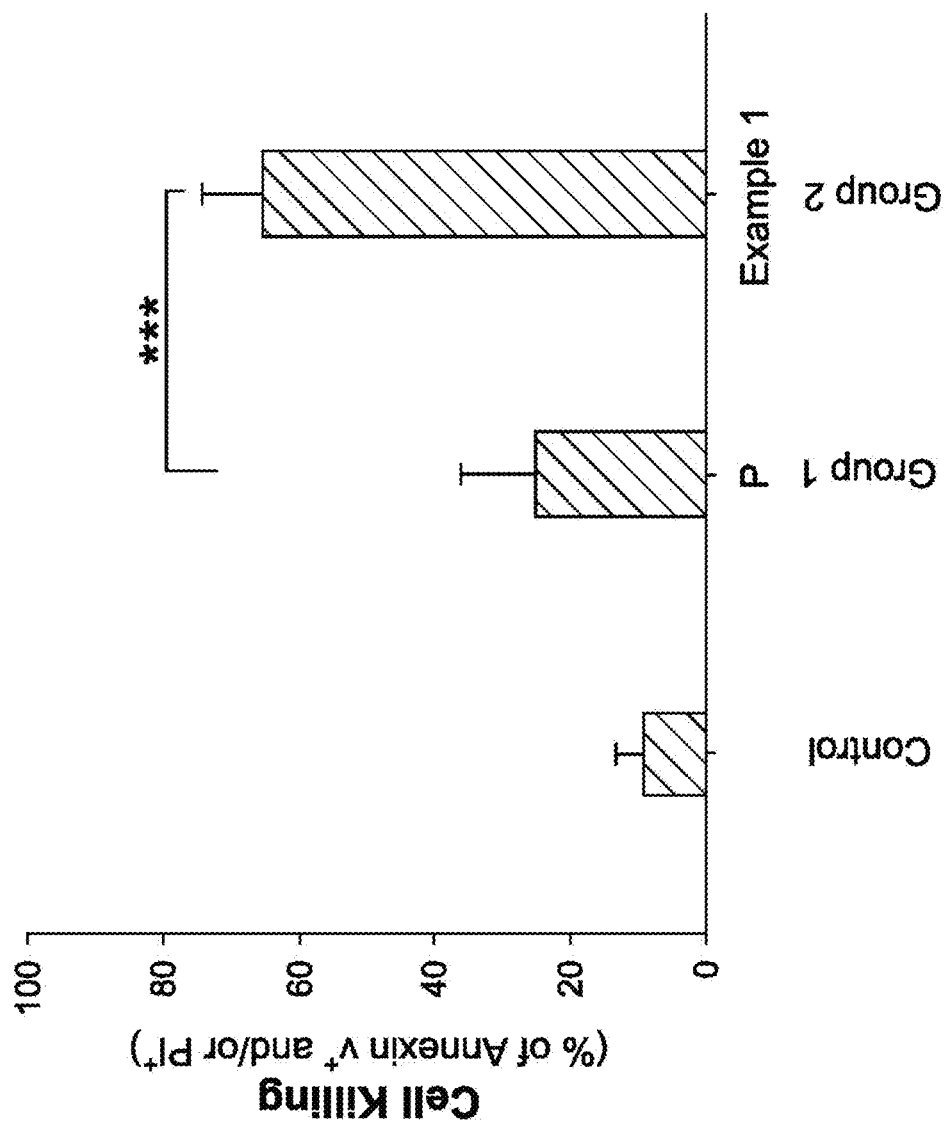
Figure 4E:
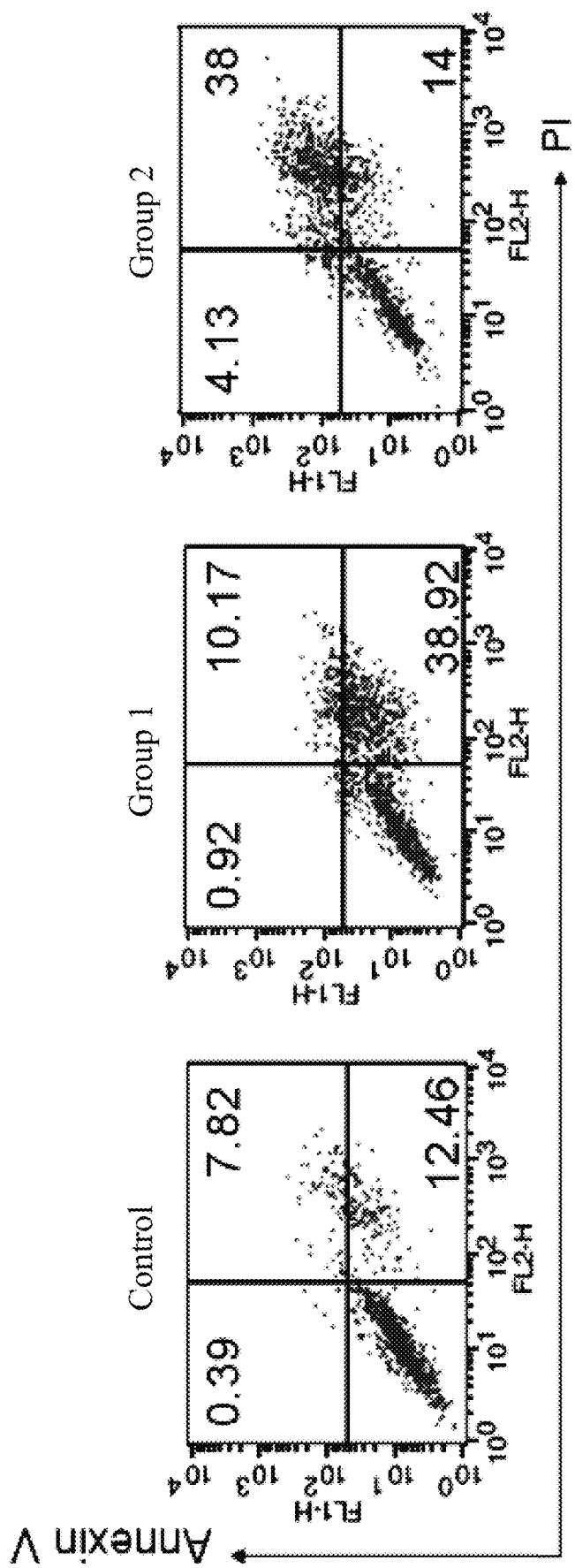
Figure 4F:
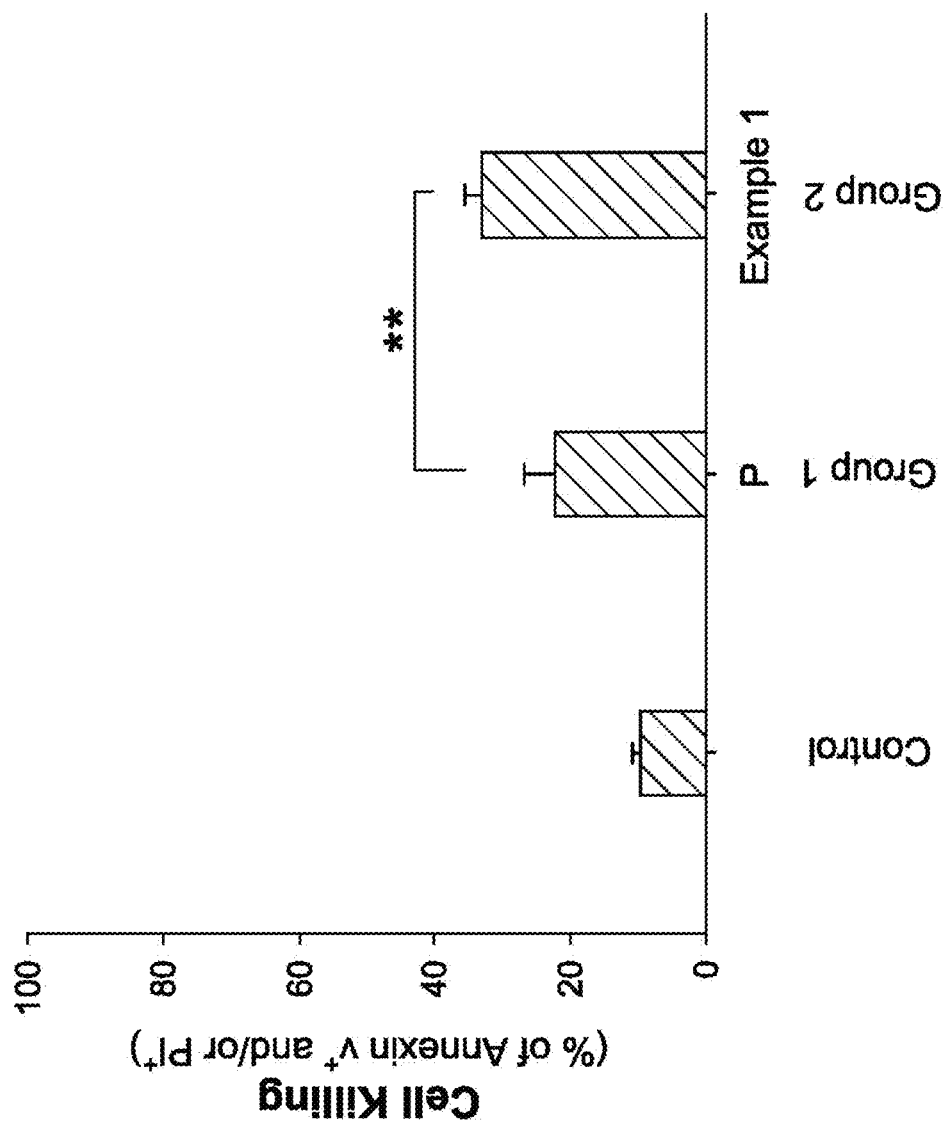
Figure 4G:
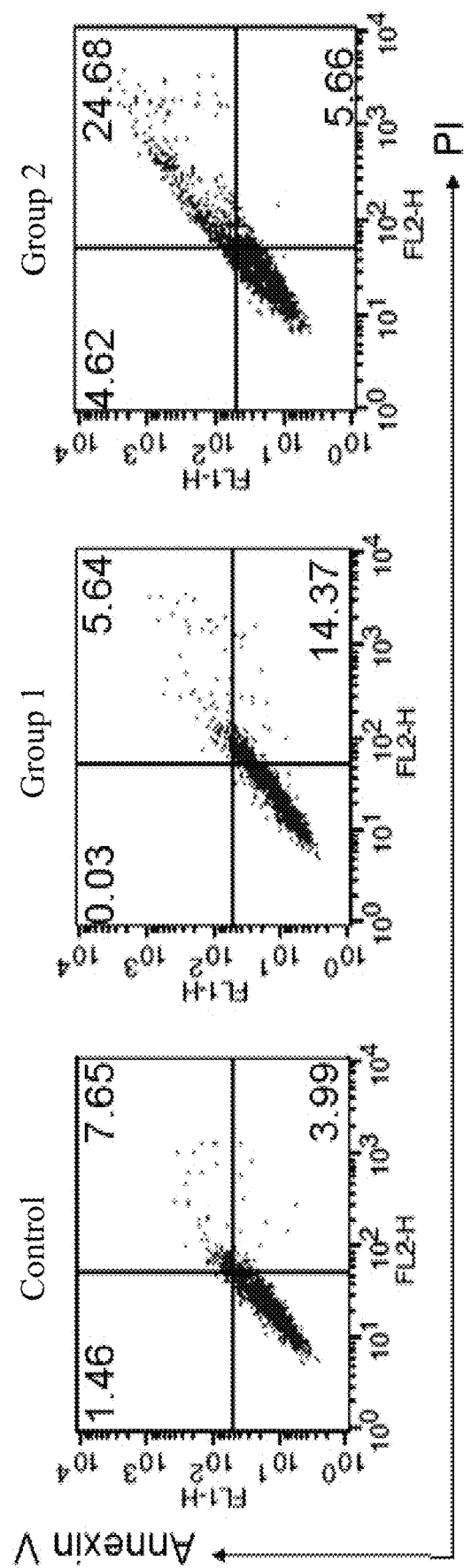
Figure 4H:
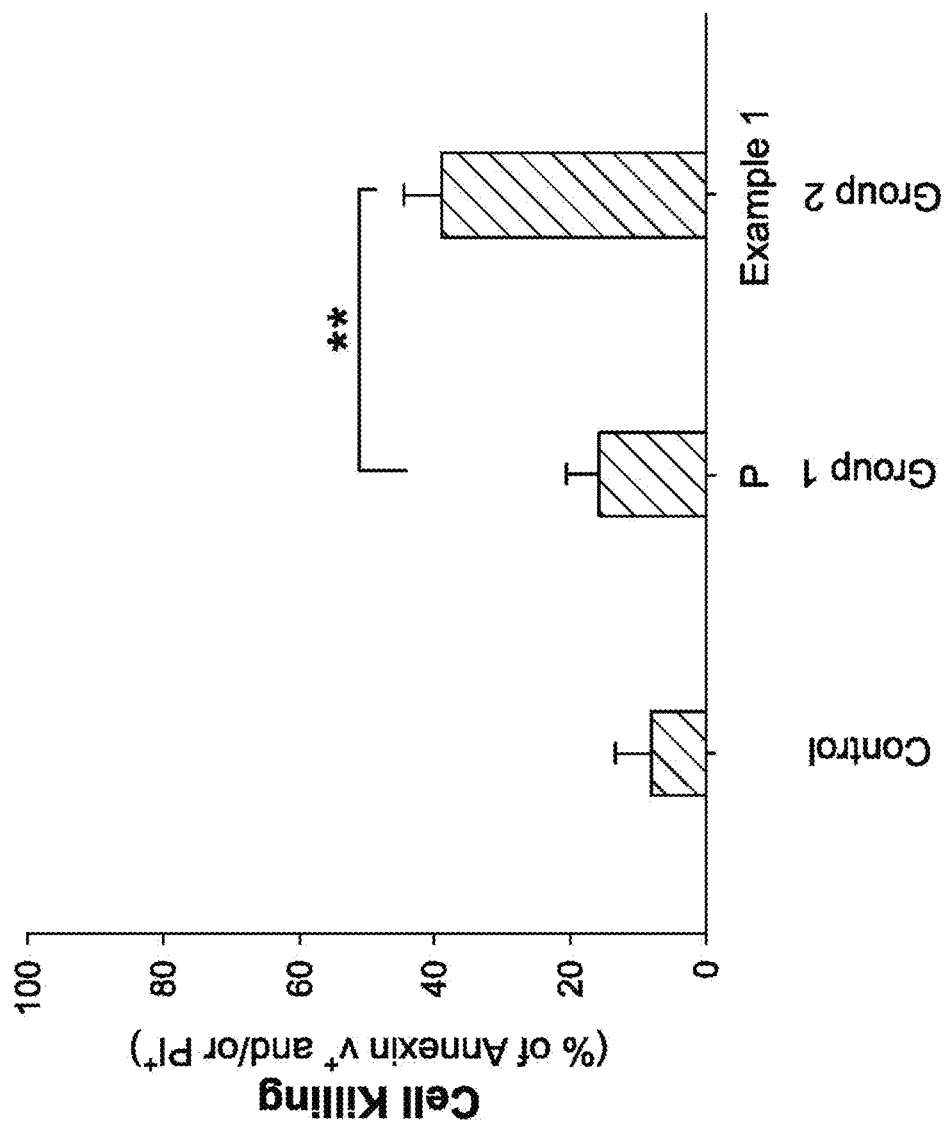
Figure 4I:
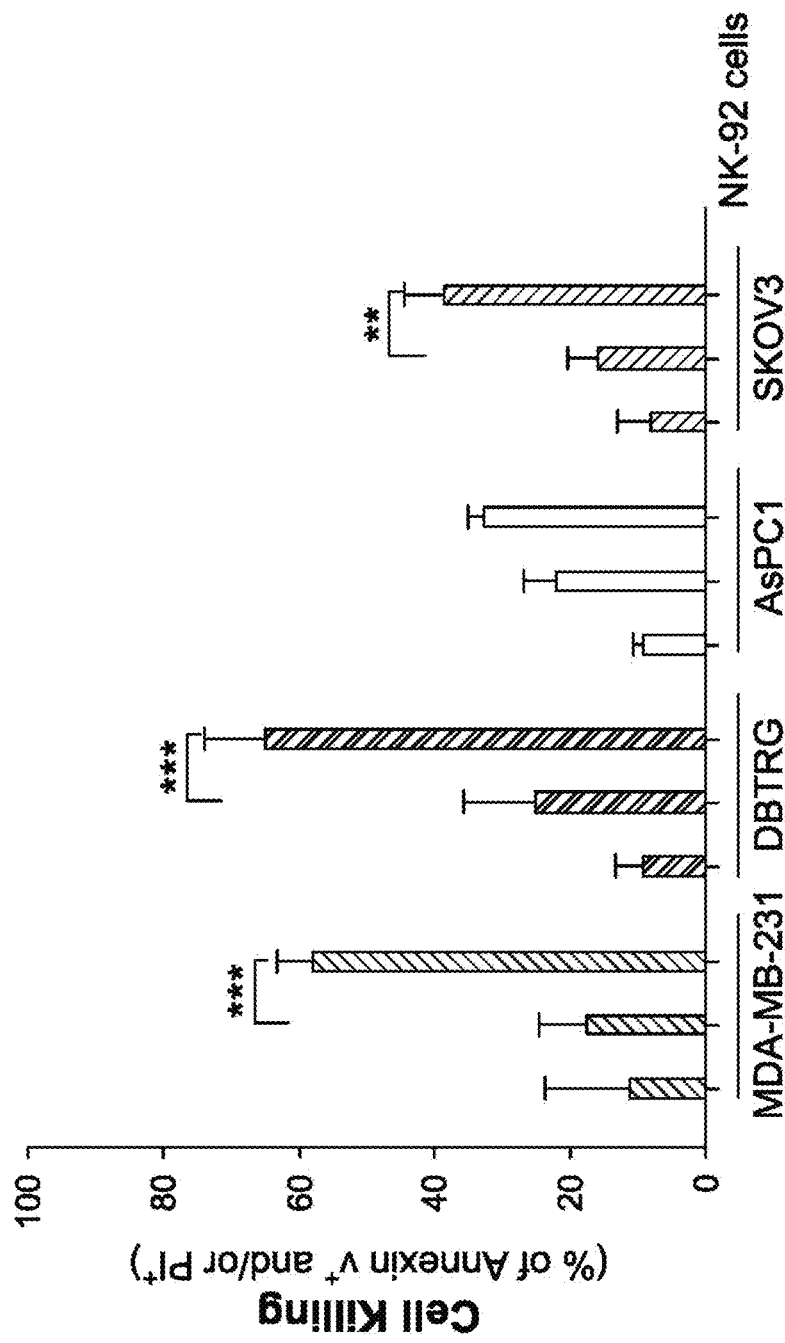

FIGS. 4A, 4B, 4C, 4D, 4E, 4F, 4G, 4H and 4I show analytical results of tumor cell death induced by the chimeric antigen receptor expressing cells according to Example 1 of the present disclosure. FIG. 4A is a graph showing the analytical results of the death of the human breast cancer cell line MDA-MB-231 induced by the chimeric antigen receptor expressing cell of Example 1, and FIG. 4B is a statistical chart of FIG. 4A after the three independent trials. FIG. 4C is a graph showing the analytical results of the death of the human malignant brain tumor cell line DBTRG induced by the chimeric antigen receptor expressing cell of Example 1, and FIG. 4D is a statistical chart of FIG. 4C after the three independent trials. FIG. 4E is a graph showing the analytical results of the death of the human pancreatic cancer cell line AsPC1 induced by the chimeric antigen receptor expressing cell of Example 1, and FIG. 4F is a statistical chart of FIG. 4E after the three independent trials. FIG. 4G is a graph showing the analytical results of the death of the human ovarian cancer cell line SKOV3 induced by the chimeric antigen receptor expressing cell of Example 1, and FIG. 4H is a statistical chart of FIG. 4G after the three independent trials. FIG. 4I is a statistical chart of FIGS. 4A, 4C, 4E and 4G after the three independent trials, wherein P represents the parental NK-92 cell line, and H represents the chimeric antigen receptor expressing cell of Example 1.

Please refer to FIGS. 4A and 4B. In the control, the death rate of the human breast cancer cell line MDA-MB-231 is only about 10%. In the group 1 treated with the parental NK-92 cell line, the death rate of the human breast cancer cell line MDA-MB-231 is increased, but there is no statistically significant difference compared to the control. In the group 2 treated with the chimeric antigen receptor expressing cell of Example 1, the death rate of the human breast cancer cell line MDA-MB-231 is about 60%, and there is a statistically significant difference ($p<0.001$) compared to the group 1.

Please refer to FIGS. 4C and 4D. In the control, the death rate of the human malignant brain tumor cell line DBTRG is less than 10%. In the group 1 treated with the parental NK-92 cell line, the death rate of the human malignant brain tumor cell line DBTRG is increased, but there is no statistically significant difference compared to the control. In the group 2 treated with the chimeric antigen receptor expressing cell of Example 1, the death rate of the human malignant brain tumor cell line DBTRG is more than 60%, and there is a statistically significant difference ($p<0.001$) compared to the group 1.

Please refer to FIGS. 4E and 4F. In the control, the death rate of the human pancreatic cancer cell line AsPC1 is less than 10%. In the group 1 treated with the parental NK-92 cell line, the death rate of the human pancreatic cancer cell line AsPC1 is increased, but there is no statistically significant difference compared to the control. In the group 2 treated with the chimeric antigen receptor expressing cell of Example 1, the death rate of the human pancreatic cancer cell line AsPC1 is approximately 40%, and there is a statistically significant difference ($p<0.01$) compared to the group 1.

Please refer to FIGS. 4G and 4H. In the control, the death rate of the human ovarian cancer cell line SKOV3 is less than 10%. In the group 1 treated with the parental NK-92 cell line, the death rate of the human ovarian cancer cell line SKOV3 is increased, but there is no statistically significant difference compared to the control. In the group 2 treated with the chimeric antigen receptor expressing cell of Example 1, the death rate of the human ovarian cancer cell line SKOV3 is approximately 40%, and there is a statistically significant difference ($p<0.01$) compared to the group 1.

Please refer to FIG. 4I, the results indicate that the chimeric antigen receptor expressing cell of Example 1 can be used to treat with the human breast cancer cell line MDA-MB-231, the human malignant brain tumor cell line DBTRG, the human pancreatic cancer cell line AsPC1 and the human ovarian cancer cell line SKOV3 for excellent cell killing. Therefore, the chimeric antigen receptor expressing cell of the present disclosure can be used for inhibiting the proliferation of the tumor cells in the subject in need for the treatment of the tumor. Preferably, the tumor cell can be the breast cancer cell, the polymorphic glioblastoma cell, the pancreatic cancer cell or the ovarian cancer cell.

2.2. Example 2

Figure 5:
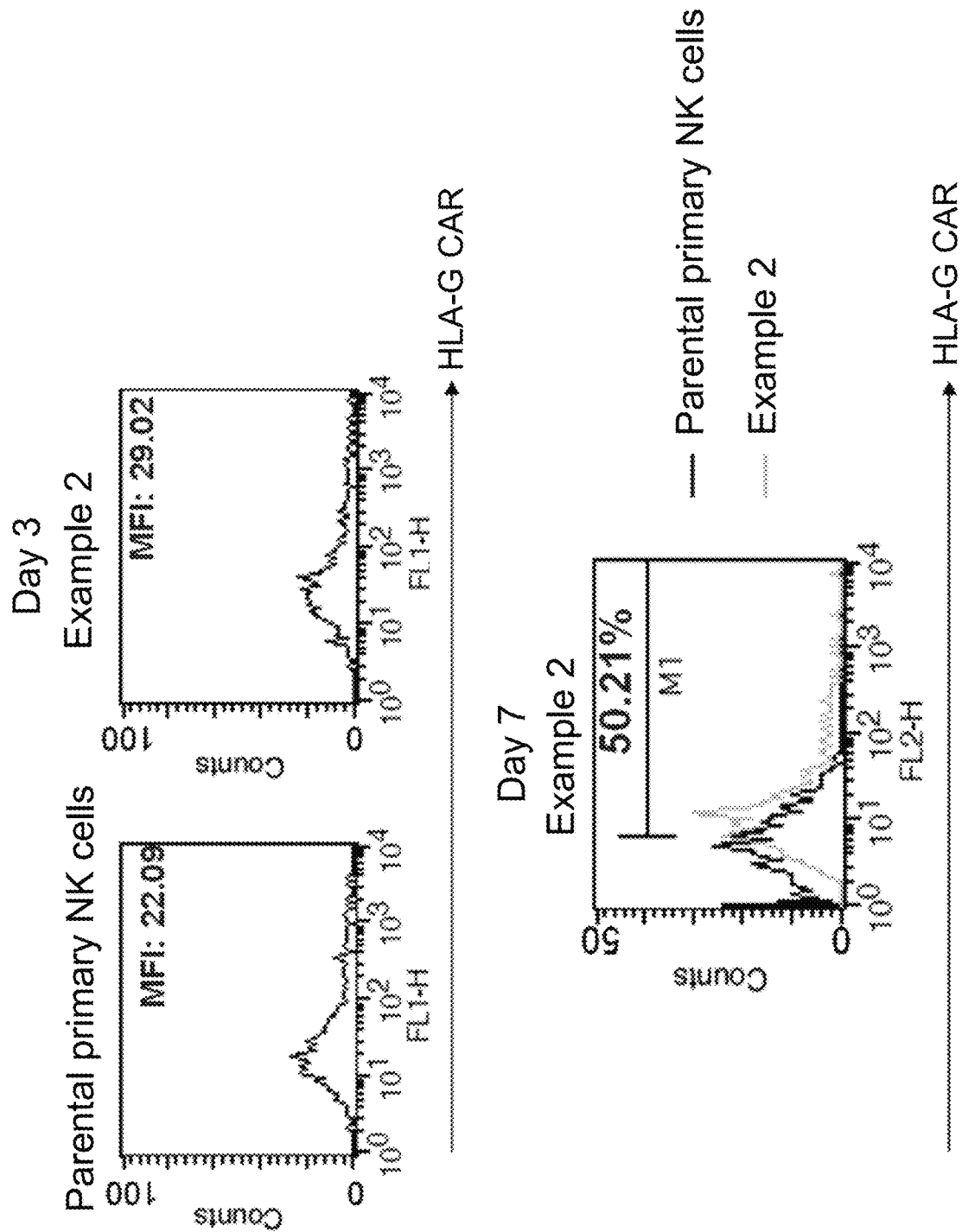
FIG. 5 is a graph showing an expression level of chimeric antigen receptors in a chimeric antigen receptor expressing cell according to Example 2 of the present disclosure.

The chimeric antigen receptor of the present disclosure is transduced into the primary NK cell to obtain the chimeric antigen receptor expressing cell of Example 2 of the present disclosure, and the expression level of the chimeric antigen receptor of the obtained chimeric antigen receptor expressing cell of Example 2 is analyzed by the flow cytometry. Please refer to FIG. 5, which is a graph showing an expression level of chimeric antigen receptors in a chimeric antigen receptor expressing cell according to Example 2 of the present disclosure. FIG. 5 shows the expression level of the chimeric antigen receptor of the parental primary NK cell without transducing the chimeric antigen receptor of the present disclosure, and the expression level of the chimeric antigen receptor of the chimeric antigen receptor expressing cell of Example 2 on day 3 and day 7 after transduction the chimeric antigen receptor. In FIG. 5, the MFI of the parental primary NK cell is 22.09%, while the MFI of the chimeric antigen receptor expressing cell of Example 2 on day 3 and day 7 after transduction can reach 29.02% and 50.21%, respectively. The results indicate that the chimeric antigen receptor expressing cell of Example 2 can stably express the chimeric antigen receptor of the present disclosure.

The effects of the chimeric antigen receptor expressing cell of Example 2 of the present disclosure on inducing the death of the breast cancer cells, the glioblastoma multiforme cells, the pancreatic cancer cells, and the ovarian cancer cells are further demonstrated in following experiments.

First, the human breast cancer cell line MDA-MB-231, the human malignant brain tumor cell line DBTRG, the human pancreatic cancer cell line AsPC1 and the human ovarian cancer cell line SKOV3 are seeded in a 12-well plate at a density of $1\times10^5$ cells/well. The cells are subsequently incubated for 24 hours. Each type of the tumor cells is divided into three groups. In a control, the tumor cells are untreated. In a group 1, the tumor cells are treated with the parental primary NK cell, and the number of the parental primary NK cell treated is 1×10$^5$ cells. In a group 2, the tumor cells are treated with the chimeric antigen receptor expressing cell of Example 2, and the number of the chimeric antigen receptor expressing cell of Example 2 treated is 1×10$^5$ cells. The treated cells are stained with Annexin V-FITC and propidium iodide (PI), and the apoptosis and the death of the tumor cells are detected by the flow cytometry. The sum of the percentage of cells stained with Annexin V-FITC and/or PI (that is the percentage of cells in the first quadrant, the second quadrant, and the fourth quadrant of the bivariate flow cytometry scatter plot) are calculated to obtain the cytotoxicity. The results of the cytotoxicity are counted after the three independent trials in each group.

Figure 6A:
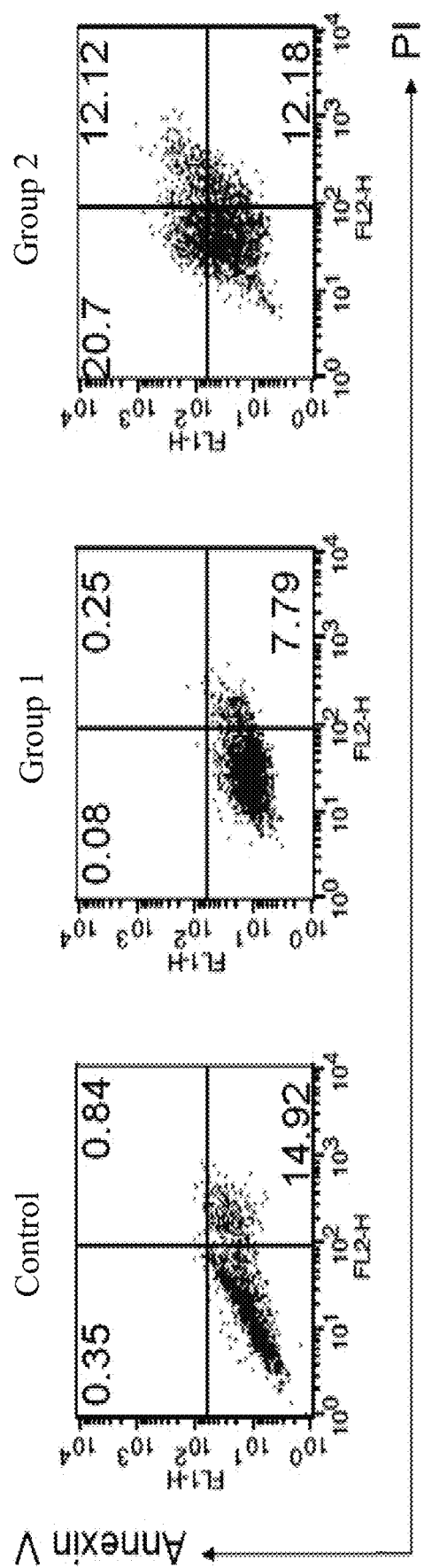
FIGS. 6A, 6B, 6C, 6D, 6E, 6F, 6G, 6H and 6I show analytical results of tumor cell death induced by chimeric antigen receptor expressing cells according to Example 2 of the present disclosure.
Figure 6B:
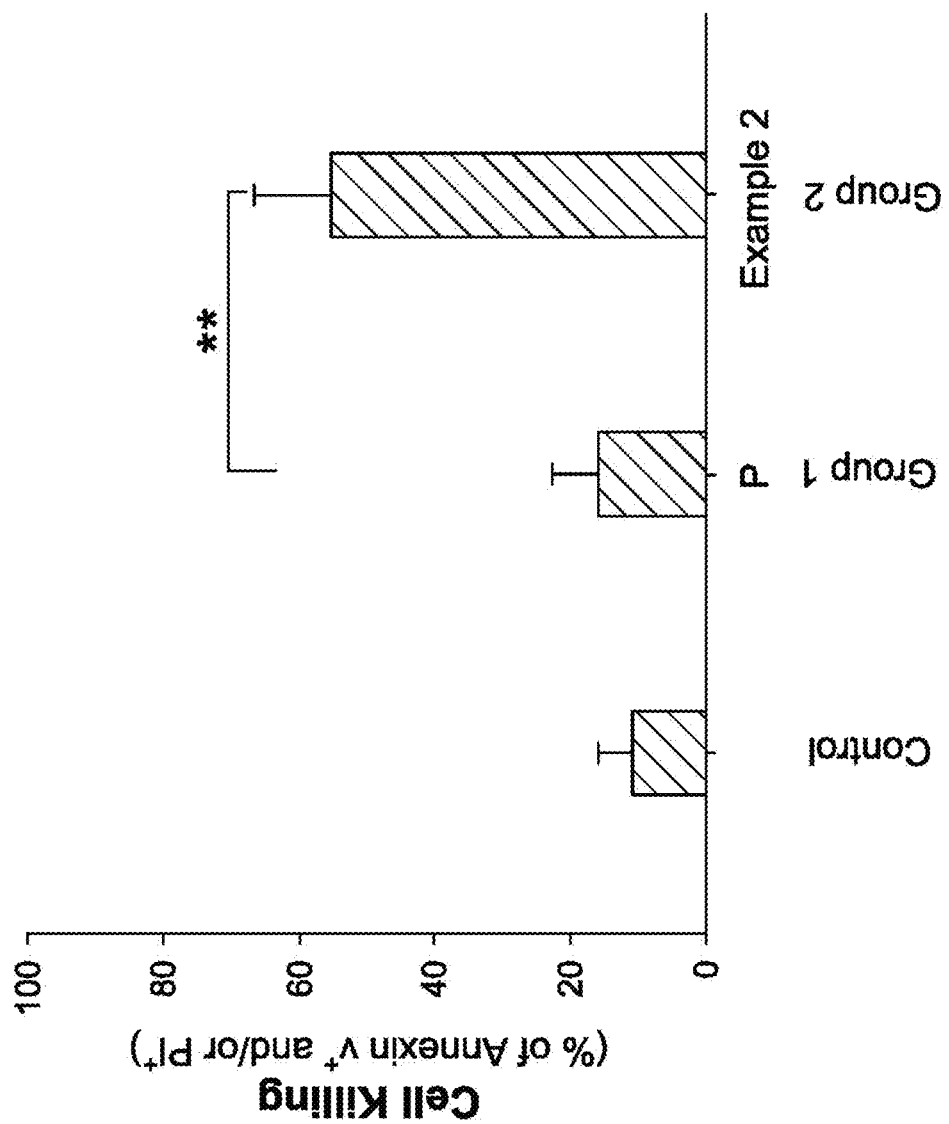
Figure 6C:
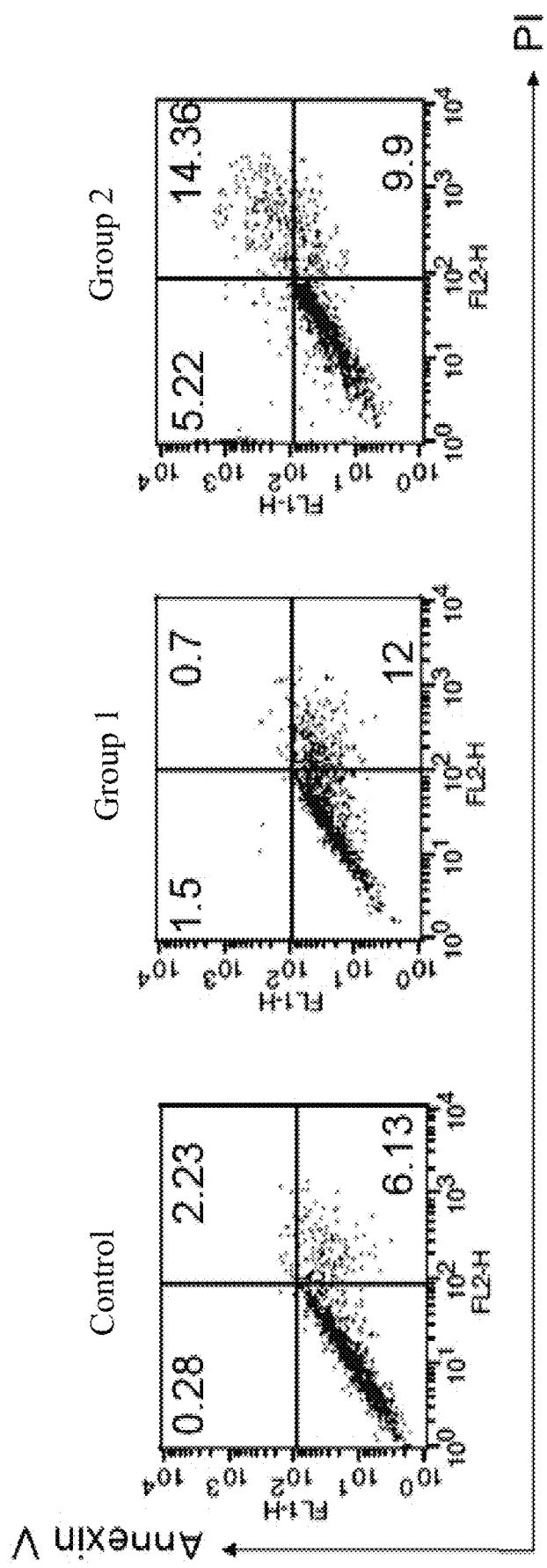
Figure 6D:
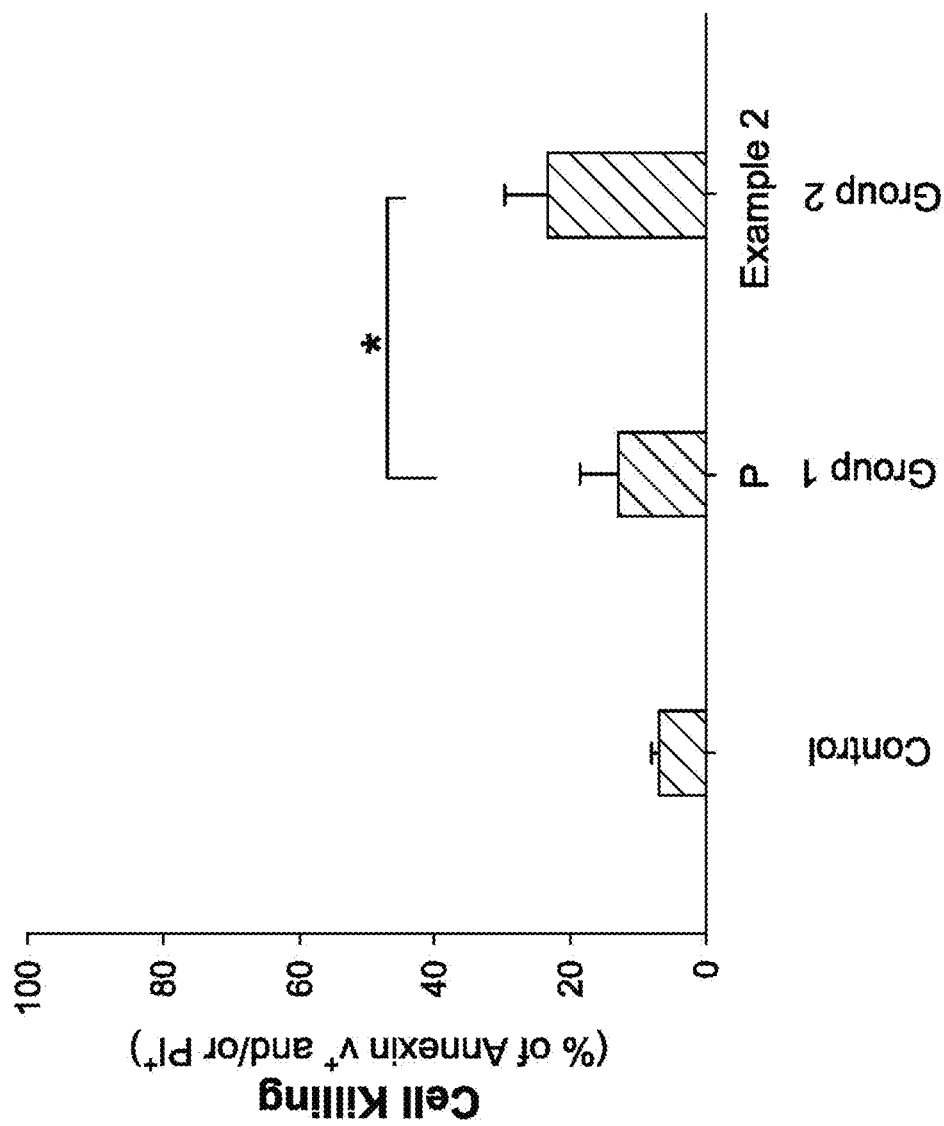
Figure 6E:
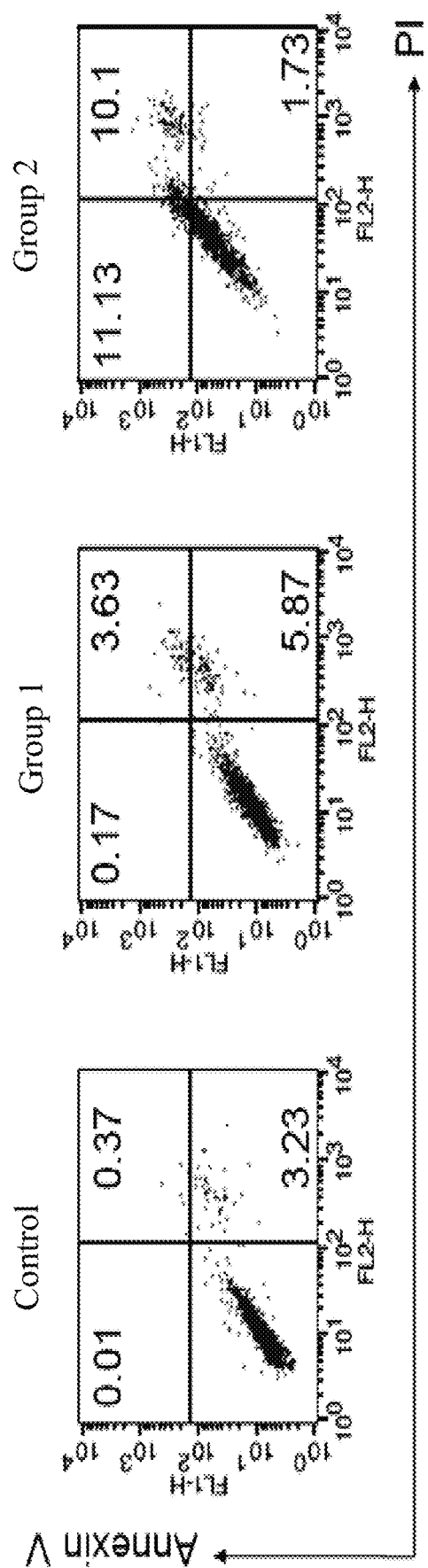
Figure 6F:
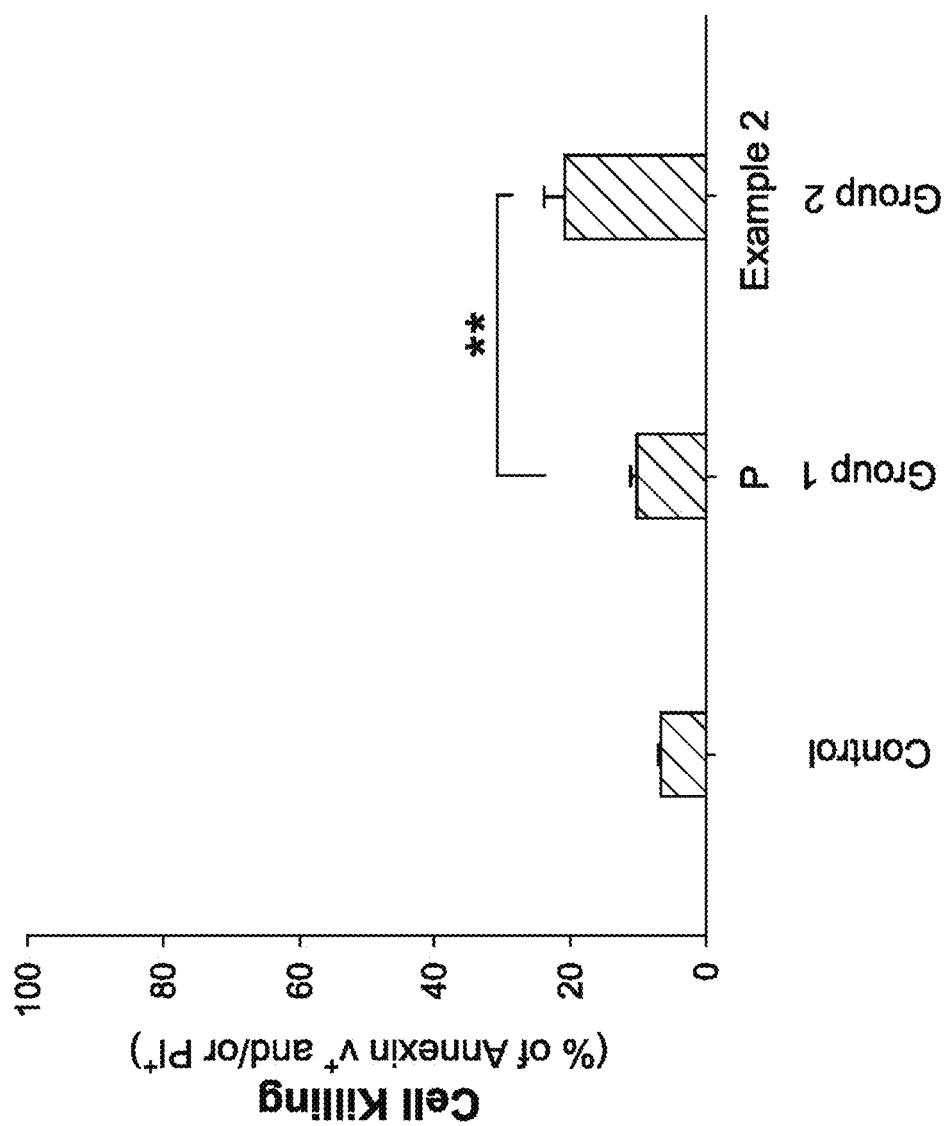
Figure 6G:
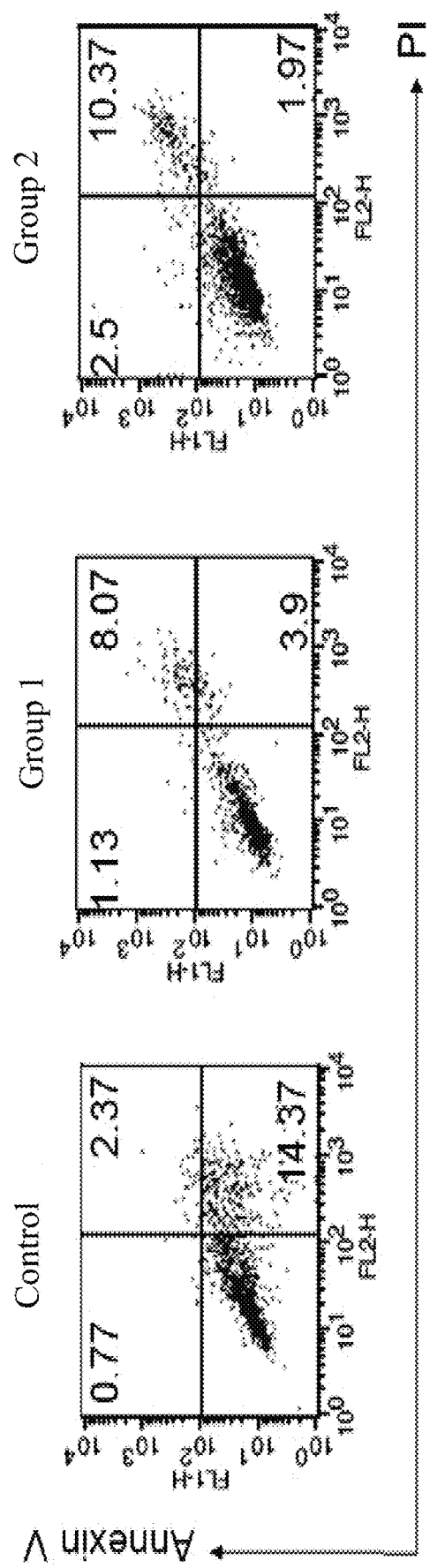
Figure 6H:
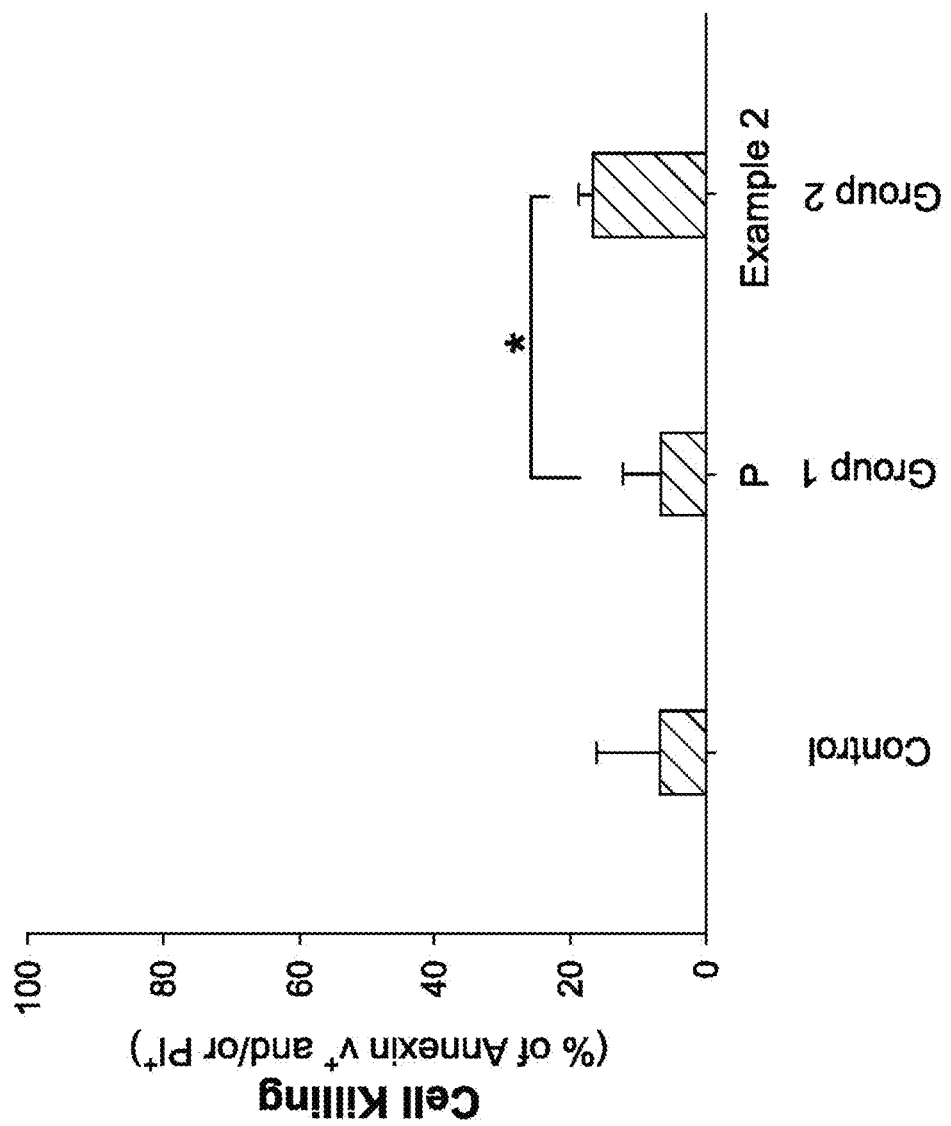
Figure 6I:
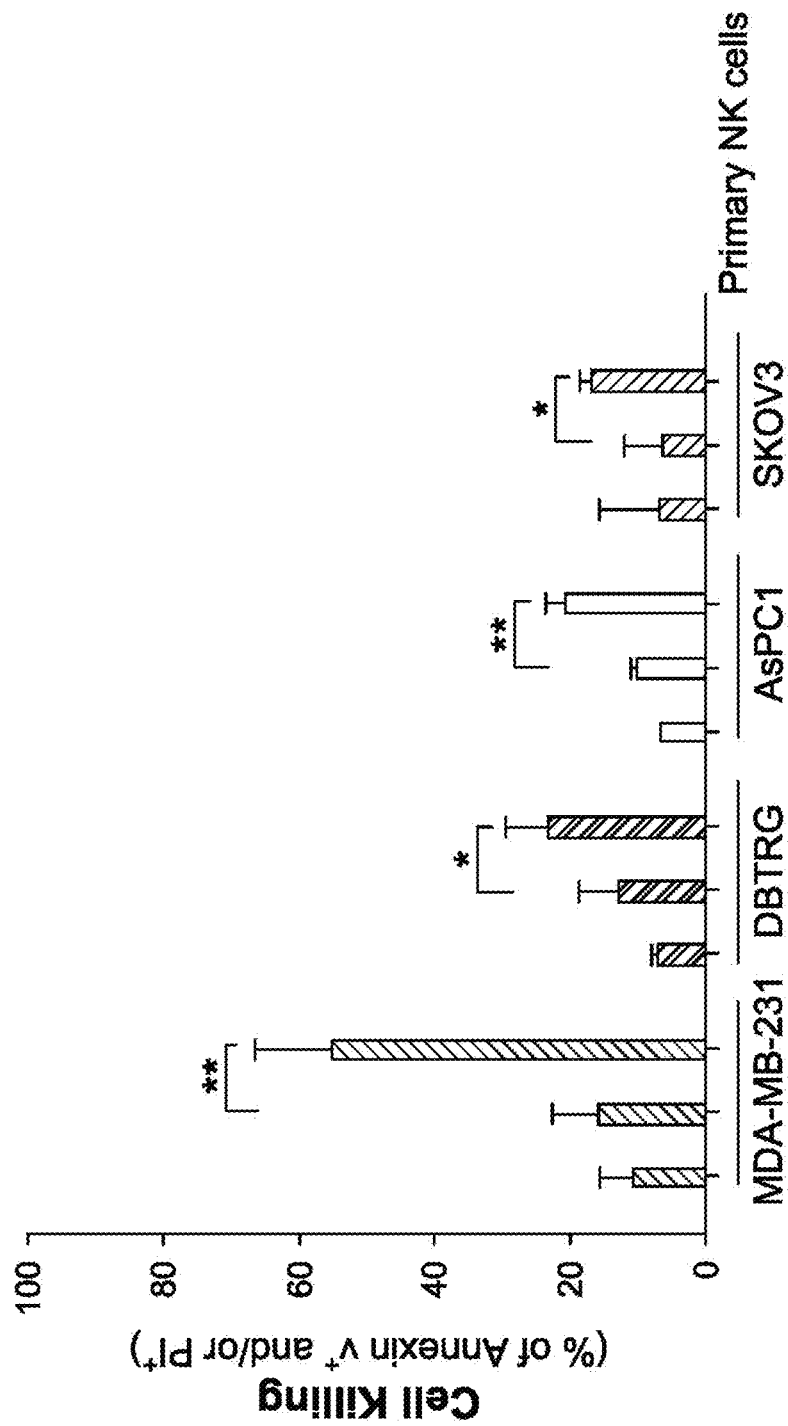

FIGS. 6A, 6B, 6C, 6D, 6E, 6F, 6G, 6H and 6I show analytical results of tumor cell death induced by the chimeric antigen receptor expressing cells according to Example 2 of the present disclosure. FIG. 6A is a graph showing the analytical results of the death of the human breast cancer cell line MDA-MB-231 induced by the chimeric antigen receptor expressing cell of Example 2, and FIG. 6B is a statistical chart of FIG. 6A after the three independent trials. FIG. 6C is a graph showing the analytical results of the death of the human malignant brain tumor cell line DBTRG induced by the chimeric antigen receptor expressing cell of Example 2, and FIG. 6D is a statistical chart of FIG. 6C after the three independent trials. FIG. 6E is a graph showing the analytical results of the death of the human pancreatic cancer cell line AsPC1 induced by the chimeric antigen receptor expressing cell of Example 2, and FIG. 6F is a statistical chart of FIG. 6E after the three independent trials. FIG. 6G is a graph showing the analytical results of the death of the human ovarian cancer cell line SKOV3 induced by the chimeric antigen receptor expressing cell of Example 2, and FIG. 6H is a statistical chart of FIG. 6G after the three independent trials. FIG. 6I is a statistical chart of FIGS. 6A, 6C, 6E and 6G after the three independent trials, wherein P represents the parental primary NK cell, and H represents the chimeric antigen receptor expressing cell of Example 2.

Please refer to FIGS. 6A and 6B. In the control, the death rate of the human breast cancer cell line MDA-MB-231 is only about 10%. In the group 1 treated with the parental primary NK cell, the death rate of the human breast cancer cell line MDA-MB-231 is increased, but there is no statistically significant difference compared to the control. In the group 2 treated with the chimeric antigen receptor expressing cell of Example 2, the death rate of the human breast cancer cell line MDA-MB-231 is more than 50%, and there is a statistically significant difference (p<0.01) compared to the group 1.

Please refer to FIGS. 6C and 6D. In the control, the death rate of the human malignant brain tumor cell line DBTRG is less than 10%. In the group 1 treated with the parental primary NK cell, the death rate of the human malignant brain tumor cell line DBTRG is increased, but there is no statistically significant difference compared to the control. In the group 2 treated with the chimeric antigen receptor expressing cell of Example 2, the death rate of the human malignant brain tumor cell line DBTRG is more than 20%, and there is a statistically significant difference (p<0.05) compared to the group 1.

Please refer to FIGS. 6E and 6F. In the control, the death rate of the human pancreatic cancer cell line AsPC1 is less than 10%. In the group 1 treated with the parental primary NK cell, the death rate of the human pancreatic cancer cell line AsPC1 is increased, but there is no statistically significant difference compared to the control. In the group 2 treated with the chimeric antigen receptor expressing cell of Example 2, the death rate of the human pancreatic cancer cell line AsPC1 is approximately 20%, and there is a statistically significant difference (p<0.01) compared to the group 1.

Please refer to FIGS. 6G and 6H. In the control, the death rate of the human ovarian cancer cell line SKOV3 is less than 10%. In the group 1 treated with the parental primary NK cell, the death rate of the human ovarian cancer cell line SKOV3 is comparable to that of the control. In the group 2 treated with the chimeric antigen receptor expressing cell of Example 2, the death rate of the human ovarian cancer cell line SKOV3 is approximately 20%, and there is a statistically significant difference (p<0.05) compared to the group 1.

Please refer to FIG. 6I, the results indicate that the chimeric antigen receptor expressing cell of Example 2 can be used to treat with the breast cancer cell, the polymorphic glioblastoma cell, the pancreatic cancer cell or the ovarian cancer cell for excellent cell killing. Therefore, the chimeric antigen receptor expressing cell of the present disclosure can be used for inhibiting the proliferation of the tumor cells in the subject in need for the treatment of the tumor.

2.3. Example 3

Figure 7:
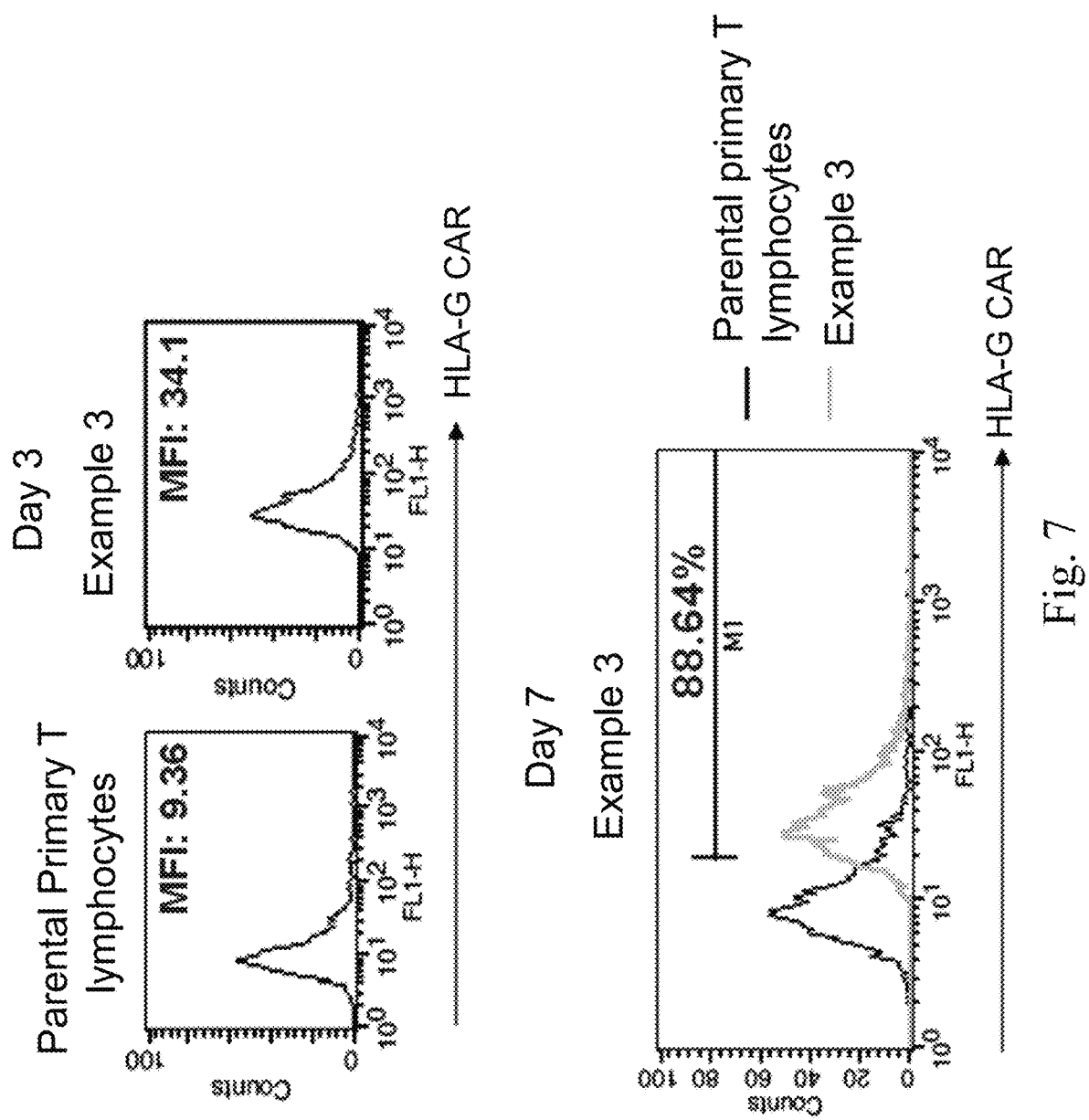
FIG. 7 is a graph showing an expression level of a chimeric antigen receptor in a chimeric antigen receptor expressing cell according to Example 3 of the present disclosure.

The chimeric antigen receptor of the present disclosure is transduced into the primary T lymphocyte to obtain the chimeric antigen receptor expressing cell of Example 3 of the present disclosure, and the expression level of the chimeric antigen receptor of the obtained chimeric antigen receptor expressing cell of Example 3 is analyzed by the flow cytometry. Please refer to FIG. 7, which is a graph showing an expression level of a chimeric antigen receptor in a chimeric antigen receptor expressing cell according to Example 3 of the present disclosure. FIG. 7 shows the expression level of the chimeric antigen receptor of the parental primary T lymphocyte without transducing the chimeric antigen receptor of the present disclosure, and the expression level of the chimeric antigen receptor of the chimeric antigen receptor expressing cell of Example 3 on day 3 and day 7 after transduction the chimeric antigen receptor. In FIG. 7, the MFI of the parental primary T lymphocyte only is 9.36%, while the MFI of the chimeric antigen receptor expressing cell of Example 3 on day 3 and day 7 after transduction can reach 34.1% and 88.64%, respectively. The results indicate that the chimeric antigen receptor expressing cell of Example 3 can stably express the chimeric antigen receptor of the present disclosure.

The effects of the chimeric antigen receptor expressing cell of Example 3 of the present disclosure on inducing the death of the breast cancer cells, the glioblastoma multiforme cells, the pancreatic cancer cells, and the ovarian cancer cells are further demonstrated in following experiments.

First, the human breast cancer cell line MDA-MB-231, the human malignant brain tumor cell line DBTRG, the human pancreatic cancer cell line AsPC1 and the human ovarian cancer cell line SKOV3 are seeded in a 12-well plate at a density of 1×10$^5$ cells/well. The cells are subsequently incubated for 24 hours. Each type of the tumor cells is divided into three groups. In a control, the tumor cells are untreated. In a group 1, the tumor cells are treated with the parental primary T lymphocyte, and the number of the parental primary T lymphocyte treated is 1×10$^5$ cells. In a group 2, the tumor cells are treated with the chimeric antigen receptor expressing cell of Example 3, and the number of the chimeric antigen receptor expressing cell of Example 3 treated is 1×10$^5$ cells. The treated cells are stained with Annexin V-FITC and propidium iodide (PI), and the apoptosis and the death of the tumor cells are detected by the flow cytometry. The sum of the percentage of cells stained with Annexin V-FITC and/or PI (that is the percentage of cells in the first quadrant, the second quadrant, and the fourth quadrant of the bivariate flow cytometry scatter plot) are calculated to obtain the cytotoxicity. The results of the cytotoxicity are counted after the three independent trials in each group.

Figure 8A:
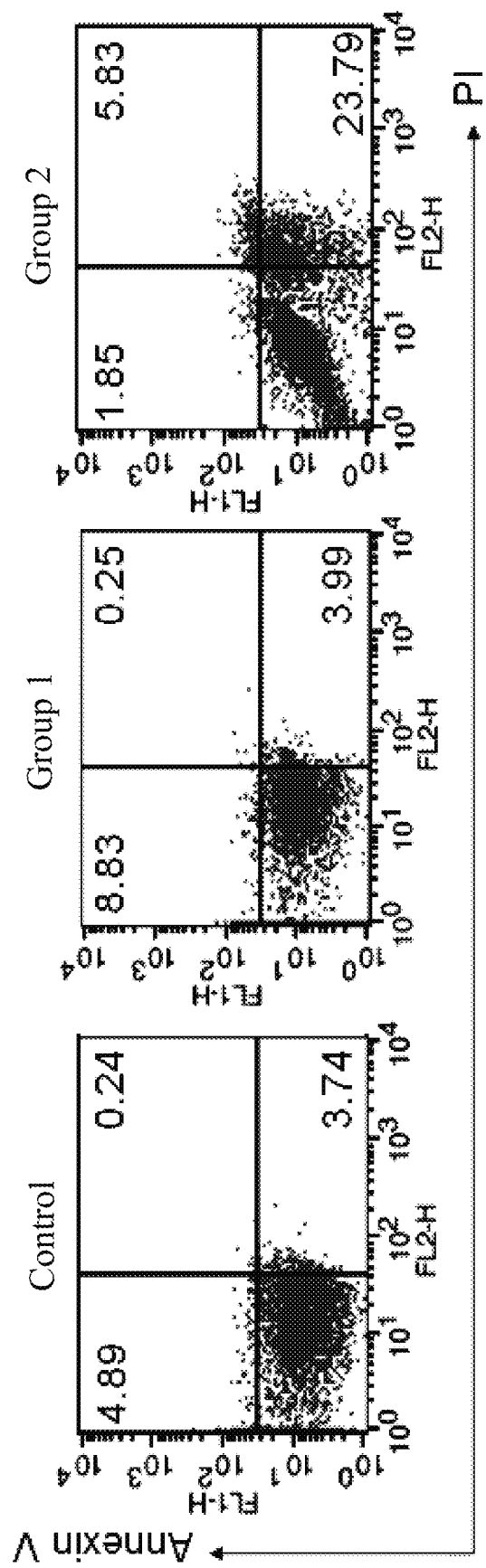
FIGS. 8A, 8B, 8C, 8D, 8E, 8F, 8G, 8H and 8I show analytical results of tumor cell death induced by chimeric antigen receptor expressing cells according to Example 3 of the present disclosure.
Figure 8B:
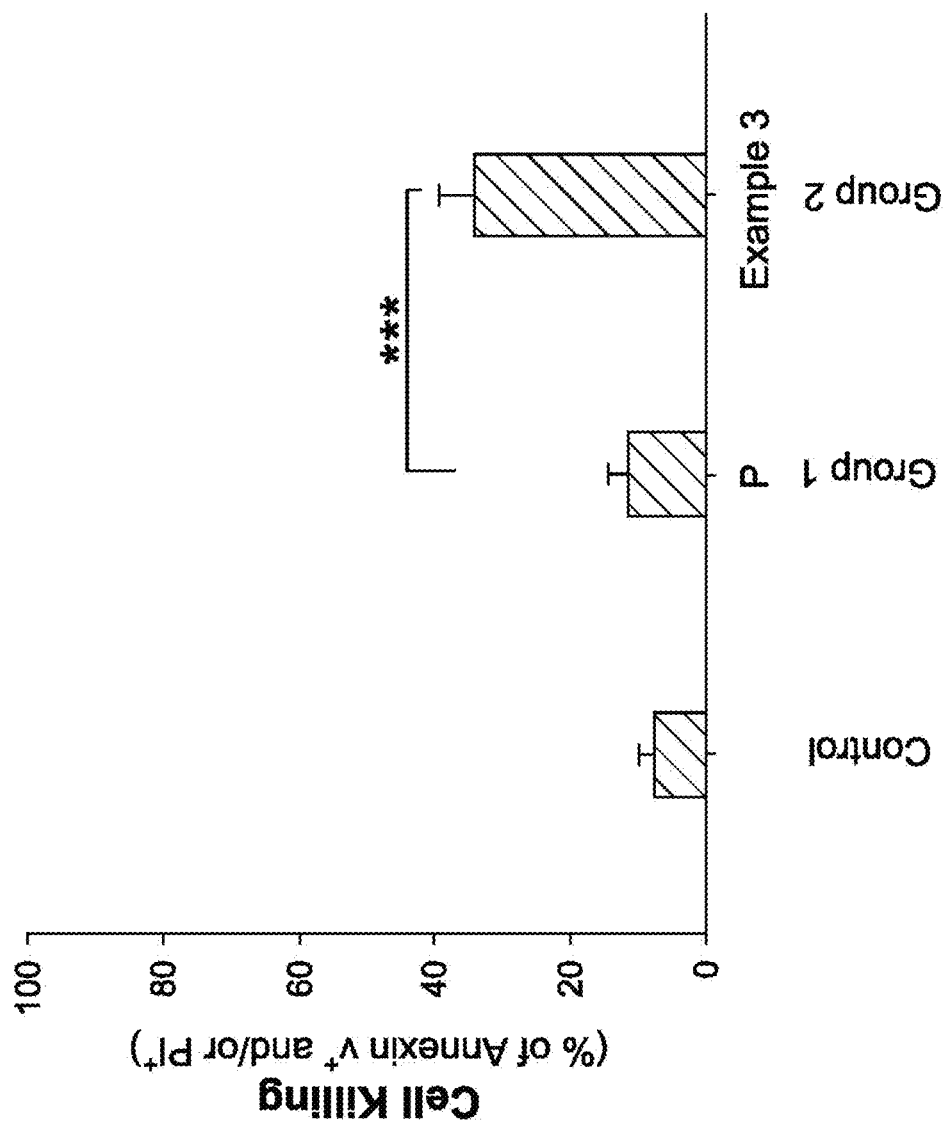
Figure 8C:
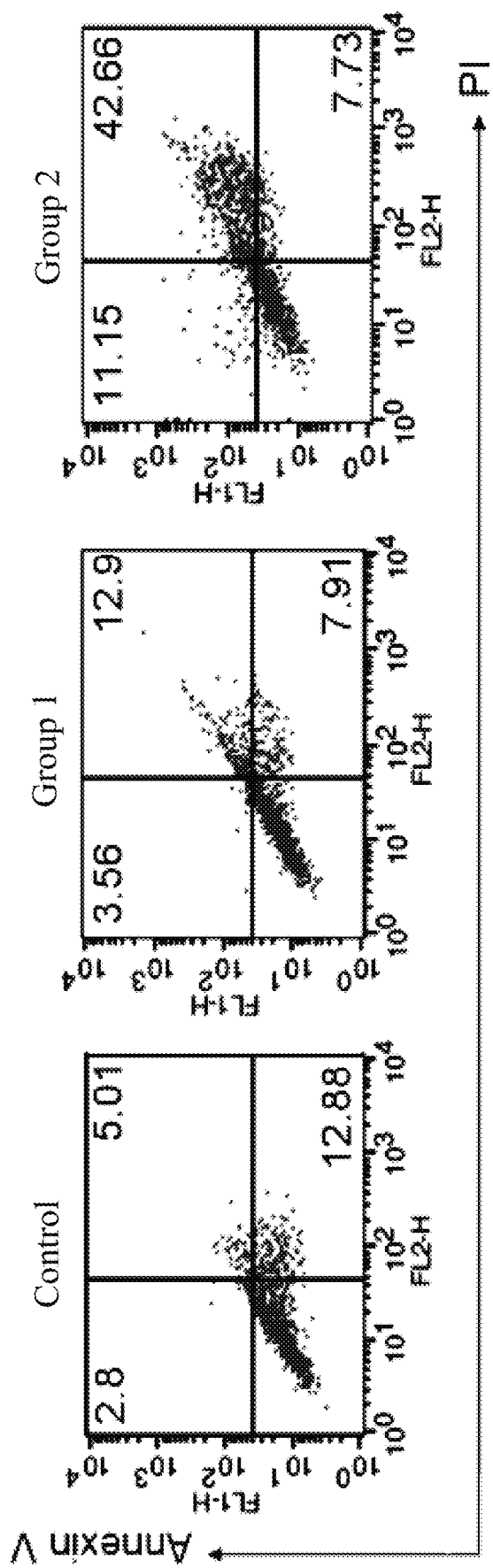
Figure 8D:
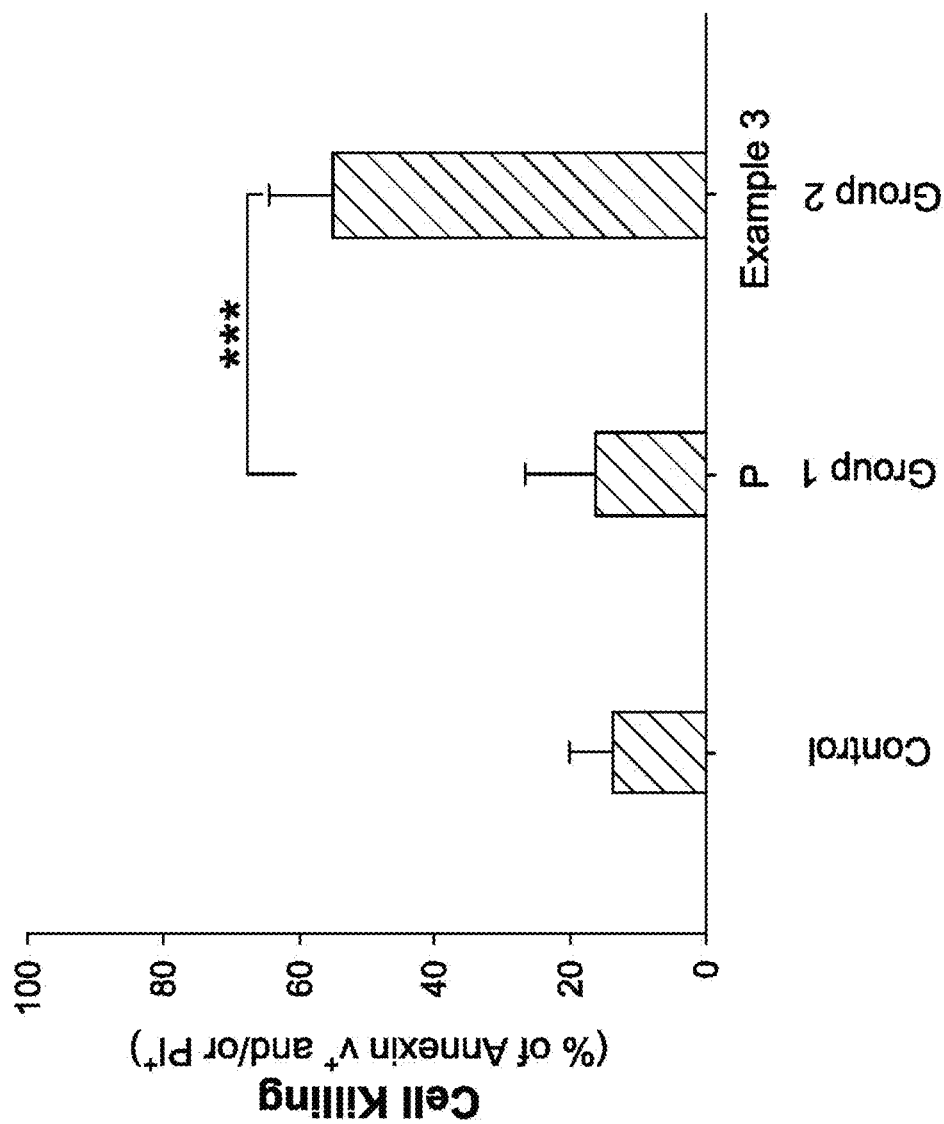
Figure 8E:
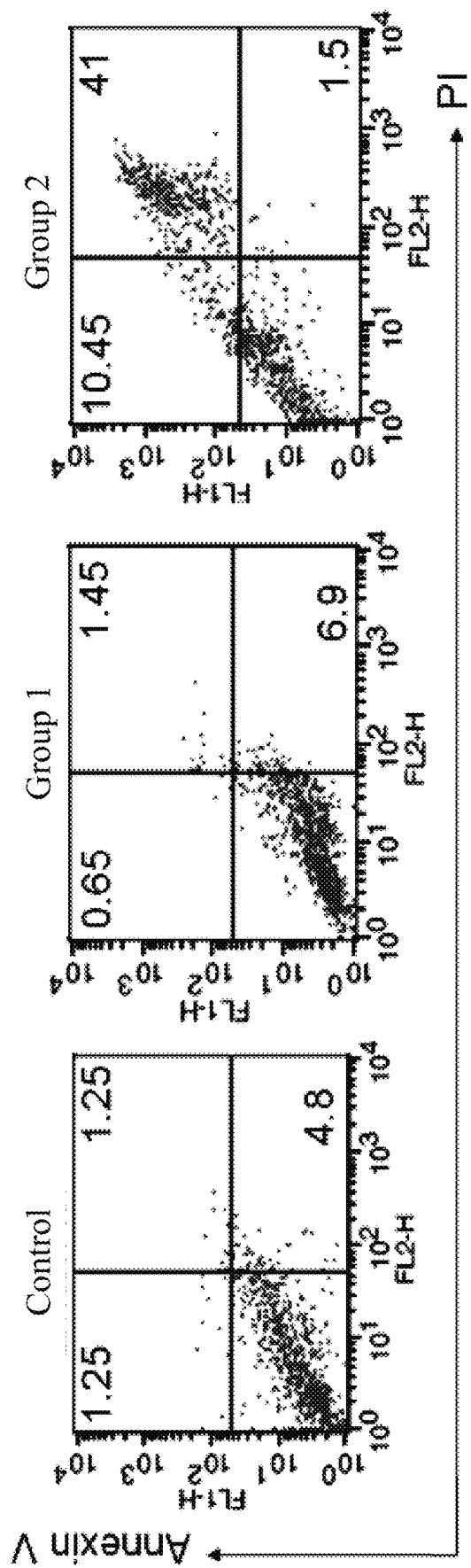
Figure 8F:
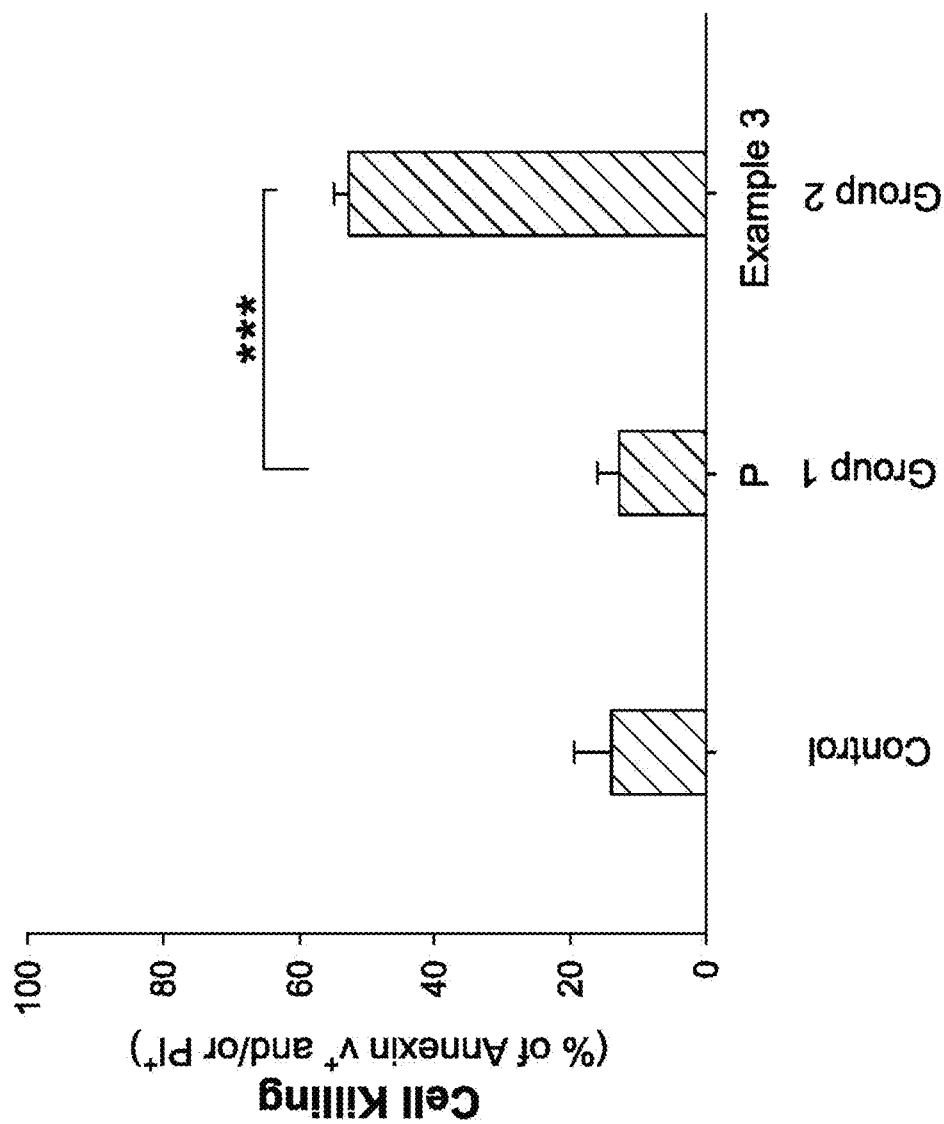
Figure 8G:
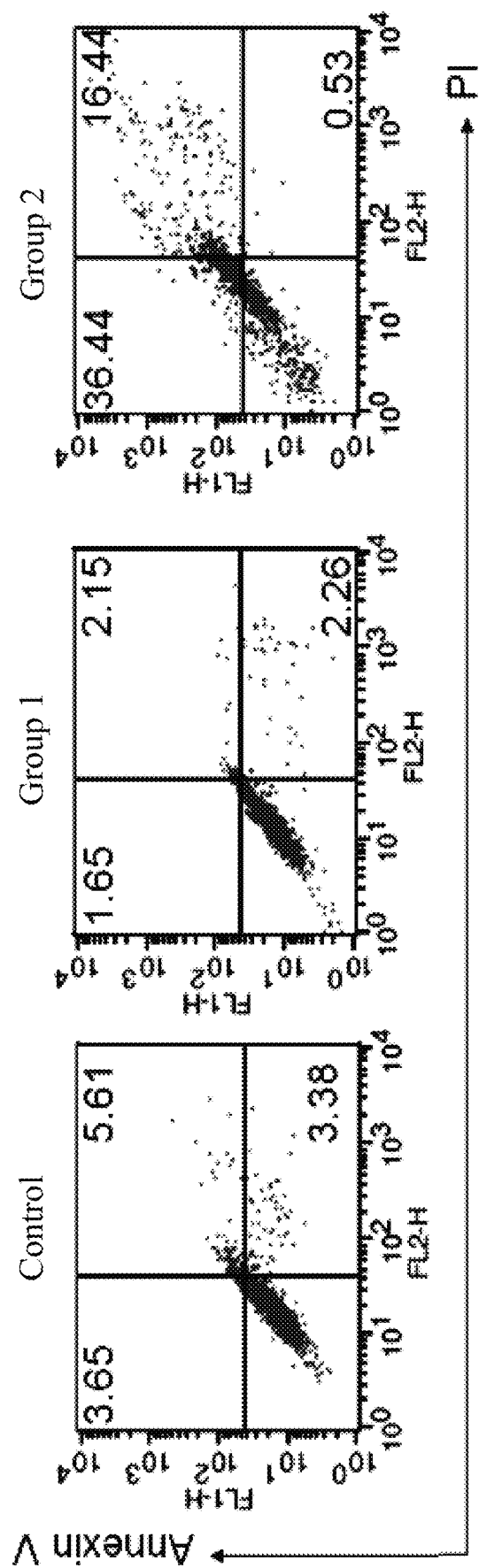
Figure 8H:
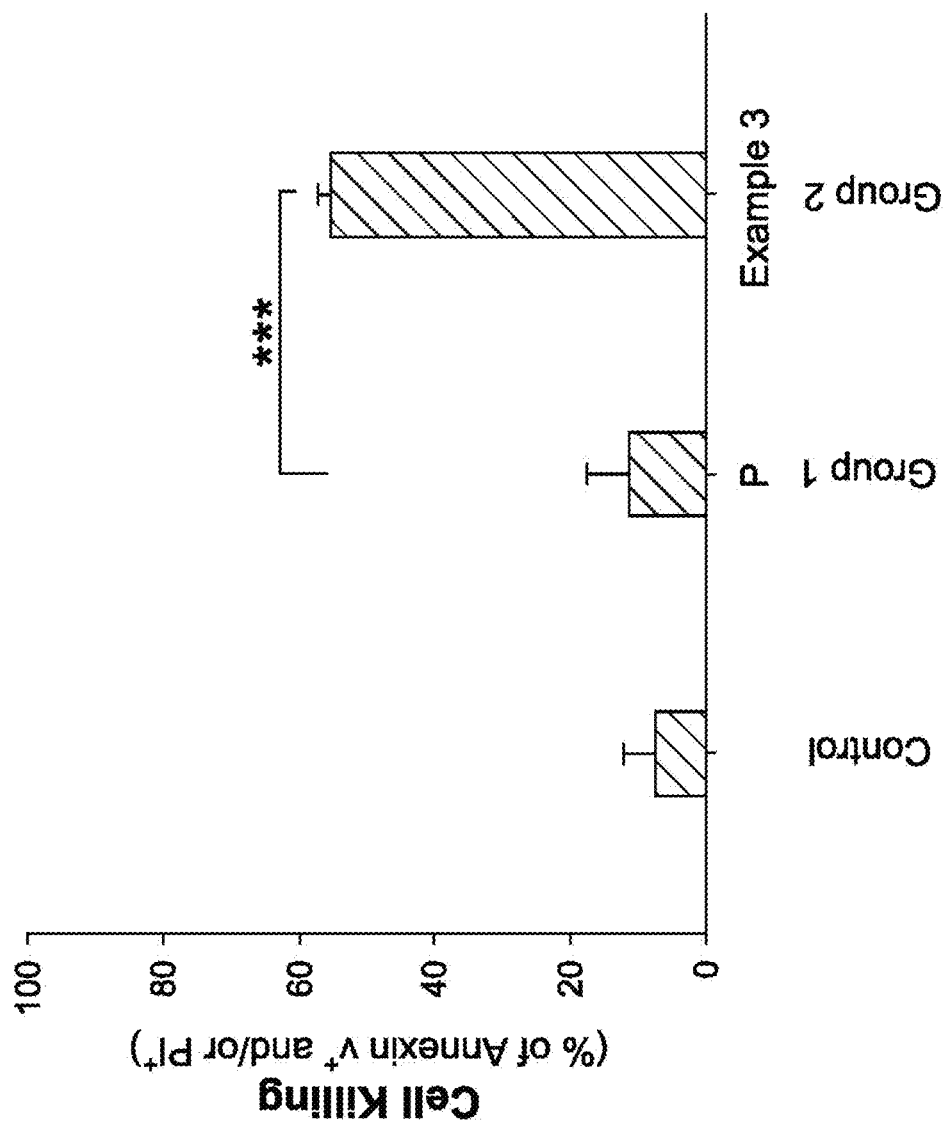
Figure 8I:
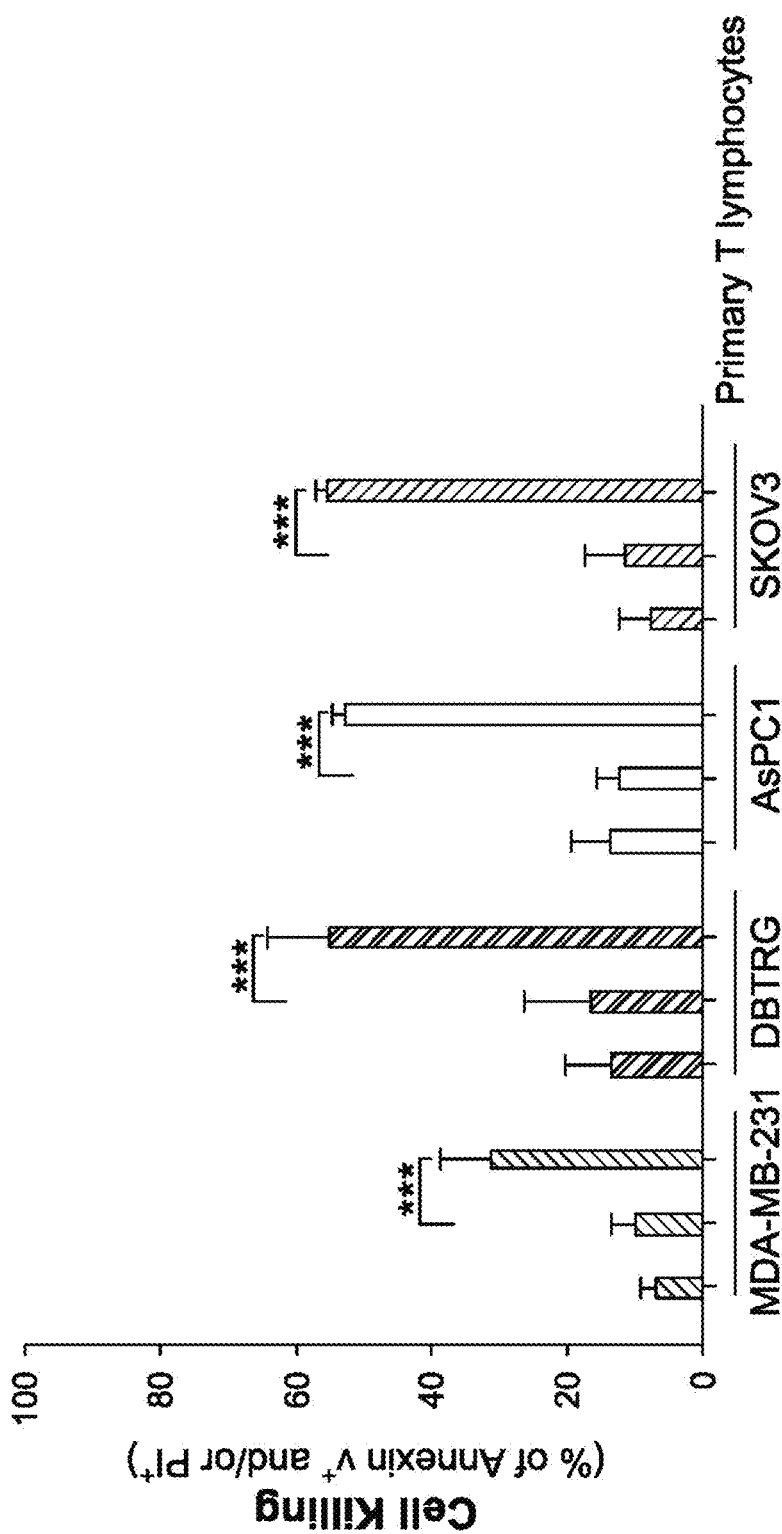

FIGS. 8A, 8B, 8C, 8D, 8E, 8F, 8G, 8H and 8I show analytical results of tumor cell death induced by the chimeric antigen receptor expressing cells according to Example 3 of the present disclosure. FIG. 8A is a graph showing the analytical results of the death of the human breast cancer cell line MDA-MB-231 induced by the chimeric antigen receptor expressing cell of Example 3, and FIG. 8B is a statistical chart of FIG. 8A after the three independent trials. FIG. 8C is a graph showing the analytical results of the death of the human malignant brain tumor cell line DBTRG induced by the chimeric antigen receptor expressing cell of Example 3, and FIG. 8D is a statistical chart of FIG. 8C after the three independent trials. FIG. 8E is a graph showing the analytical results of the death of the human pancreatic cancer cell line AsPC1 induced by the chimeric antigen receptor expressing cell of Example 3, and FIG. 8F is a statistical chart of FIG. 8E after the three independent trials. FIG. 8G is a graph showing the analytical results of the death of the human ovarian cancer cell line SKOV3 induced by the chimeric antigen receptor expressing cell of Example 3, and FIG. 8H is a statistical chart of FIG. 8G after the three independent trials. FIG. 8I is a statistical chart of FIGS. 8A, 8C, 8E and 8G after the three independent trials, wherein P represents the parental primary T lymphocyte, and H represents the chimeric antigen receptor expressing cell of Example 3.

Please refer to FIGS. 8A and 8B. In the control, the death rate of the human breast cancer cell line MDA-MB-231 is only about 10%. In the group 1 treated with the parental primary T lymphocyte, the death rate of the human breast cancer cell line MDA-MB-231 is increased, but there is no statistically significant difference compared to the control. In the group 2 treated with the chimeric antigen receptor expressing cell of Example 3, the death rate of the human breast cancer cell line MDA-MB-231 is more than 30%, and there is a statistically significant difference (p<0.001) compared to the group 1.

Please refer to FIGS. 8C and 8D. In the control, the death rate of the human malignant brain tumor cell line DBTRG is less than 20%. In the group 1 treated with the parental primary T lymphocyte, the death rate of the human malignant brain tumor cell line DBTRG is increased, but there is no statistically significant difference compared to the control. In the group 2 treated with the chimeric antigen receptor expressing cell of Example 3, the death rate of the human malignant brain tumor cell line DBTRG is more than 50%, and there is a statistically significant difference (p<0.001) compared to the group 1.

Please refer to FIGS. 8E and 8F. In the control, the death rate of the human pancreatic cancer cell line AsPC1 is less than 20%. In the group 1 treated with the parental primary T lymphocyte, the death rate of the human pancreatic cancer cell line AsPC1 is comparable to that of the control. In the group 2 treated with the chimeric antigen receptor expressing cell of Example 3, the death rate of the human pancreatic cancer cell line AsPC1 is increased to more than 50%, and there is a statistically significant difference (p<0.001) compared to the group 1.

Please refer to FIGS. 8G and 8H. In the control, the death rate of the human ovarian cancer cell line SKOV3 is less than 10%. In the group 1 treated with the parental primary T lymphocyte, the death rate of the human ovarian cancer cell line SKOV3 is increased, but there is no statistically significant difference compared to the control. In the group 2 treated with the chimeric antigen receptor expressing cell of Example 3, the death rate of the human ovarian cancer cell line SKOV3 is approximately 60%, and there is a statistically significant difference (p<0.01) compared to the group 1.

Please refer to FIG. 8I, the results indicate that the chimeric antigen receptor expressing cell of Example 3 can be used to treat with the breast cancer cell, the polymorphic glioblastoma cell, the pancreatic cancer cell or the ovarian cancer cell for excellent cell killing. Therefore, the chimeric antigen receptor expressing cell of the present disclosure can be used for inhibiting the proliferation of the tumor cells in the subject in need for the treatment of the tumor.

Figure 9:
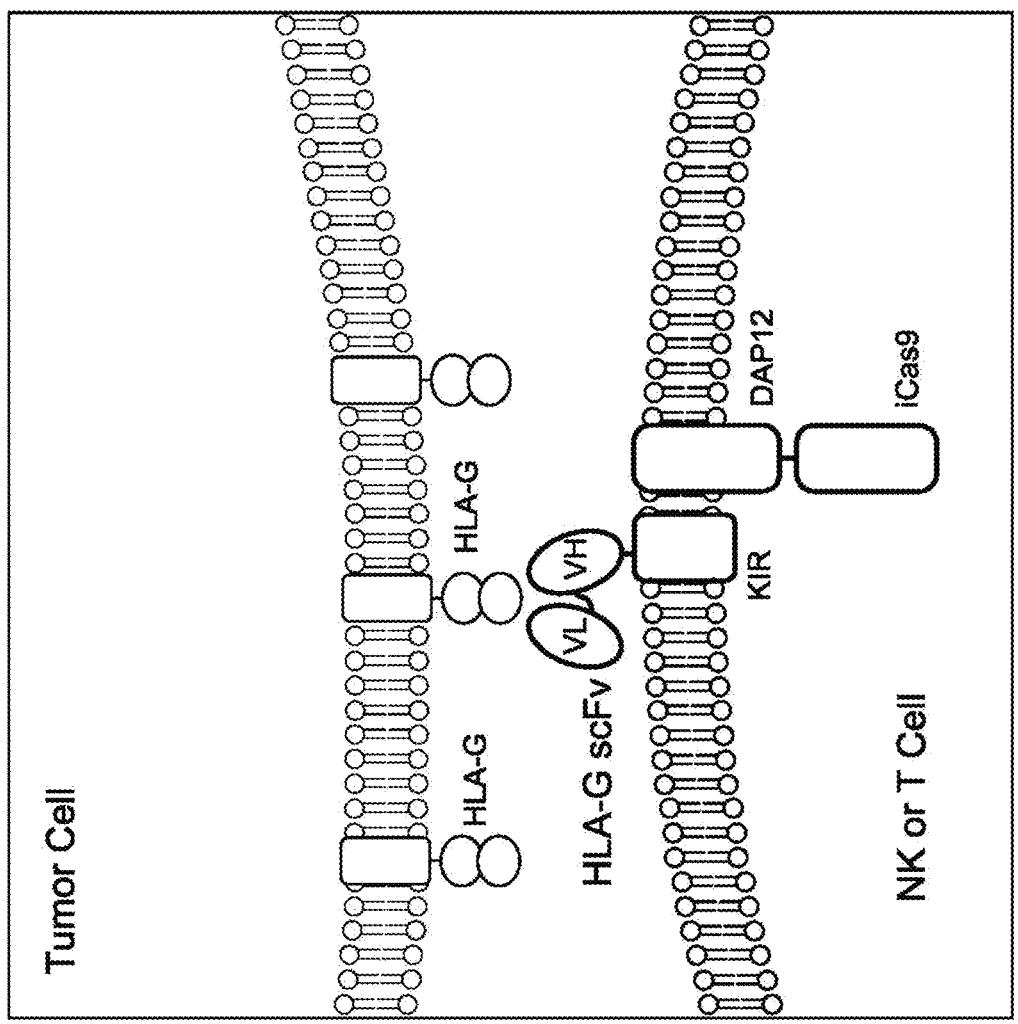
FIG. 9 is a schematic view showing the theoretical structure and mechanism of a chimeric antigen receptor in the plasma membrane of a chimeric antigen receptor expressing cell of the present disclosure.

FIG. 9 is a schematic view showing the theoretical structure and mechanism of the chimeric antigen receptor in the plasma membrane of the chimeric antigen receptor expressing cell of the present disclosure. The chimeric antigen receptor expressing cell of the present disclosure is a genetically engineered NK cell or T cell which expresses the chimeric antigen receptor of the present disclosure, and the chimeric antigen receptor of the present disclosure is a tumor-targeting receptor complex included the anti-HLA-G antibody (scFv), the HLA-G receptor (KIR) and the costimulatory domain (DAP12). Preferably, the chimeric antigen receptor of the present disclosure can further include the suicide protein iCas9. The chimeric antigen receptor expressing cell of the present disclosure can specifically recognize the HLA-G on the tumor cell membrane. When the chimeric antigen receptor expressing cell of the present disclosure binds to the HLA-G, which is specifically recognized on the surface of the tumor cell, signal transduction is triggered, and a signal cascade is generated to cause activation and proliferation of the chimeric antigen receptor expressing cell of the present disclosure. In turn, it also triggers exocytosis of lytic granules and killing of the target tumor cells.

To sum up, the chimeric antigen receptor of the present disclosure has excellent specific binding ability to the tumor cells, in particular, specific binding to HLA-G expressed on the cell membrane of tumor cells. Accordingly, the chimeric antigen receptor expressing cell of the present disclosure, which expresses the chimeric antigen receptor of the present disclosure, can specifically target the tumor cells to avoid the off-target effect, thereby effectively killing the tumor cells. Therefore, the chimeric antigen receptor expressing cell can be used for inhibiting the proliferation of the tumor cells in the subject in need for the treatment of the tumor. The pharmaceutical composition for treating the cancer includes the chimeric antigen receptor expressing cell of the present disclosure and the pharmaceutically acceptable carrier, which can effectively kill tumor cells and thereby treat cancer.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A chimeric antigen receptor expressing cell comprising:
    an immune cell, wherein the immune cell is a T lymphocyte or a natural killer (NK) cell; and
    a chimeric antigen receptor which is specific to human leukocyte antigen G (HLA-G) comprising, in order from an N-terminus to a C-terminus:
        an anti-HLA-G antibody comprising the amino acid sequence of SEQ ID NO: 1;
        an HLA-G receptor comprising the amino acid sequence of SEQ ID NO: 2;
        a 2A peptide;
        a costimulatory domain comprising the amino acid sequence of SEQ ID NO: 3; and
        a suicide protein comprising the amino acid sequence of SEQ ID NO: 4;
    wherein the 2A peptide links the HLA-G receptor and the costimulatory domain.

2. A pharmaceutical composition for treating a cancer, comprising:
    the chimeric antigen receptor expressing cell of claim 1; and
    a pharmaceutically acceptable carrier;
    wherein the cancer is a triple-negative breast cancer or a glioblastoma.

3. The pharmaceutical composition for treating a cancer of the claim 2, further comprising a chemotherapy drug.

4. A method for inhibiting proliferation of a tumor cell comprising administering a composition containing a plurality of the CAR-expressing cells of claim 1 to a subject in need of treatment of a tumor, wherein the tumor is a triple negative breast cancer cell or a glioblastoma cell.

5. The chimeric antigen receptor expressing cell of the claim 1, wherein the NK cell is a NK-92 cell line or a primary NK cell.

* * * * *